(12) United States Patent
Akiyoshi et al.

(10) Patent No.: US 12,016,570 B2
(45) Date of Patent: Jun. 25, 2024

(54) CLIP DELIVERY DEVICE

(71) Applicant: OLYMPUS CORPORATION, Tokyo (JP)

(72) Inventors: Kazuki Akiyoshi, Hirosaki (JP); Toshinori Tamura, Hirosaki (JP)

(73) Assignee: Olympus Corporation, Tokyo (JP)

(*) Notice: Subject to any disclaimer, the term of this patent is extended or adjusted under 35 U.S.C. 154(b) by 0 days.

(21) Appl. No.: 17/553,461

(22) Filed: Dec. 16, 2021

(65) Prior Publication Data

US 2022/0192673 A1  Jun. 23, 2022

Related U.S. Application Data

(60) Provisional application No. 63/130,258, filed on Dec. 23, 2020.

(51) Int. Cl.
*A61B 17/122* (2006.01)
*A61B 17/128* (2006.01)

(52) U.S. Cl.
CPC .......... *A61B 17/128* (2013.01); *A61B 17/122* (2013.01)

(58) Field of Classification Search
CPC .. A61B 2017/1225; A61B 2017/00473; A61B 17/122; A61B 17/1227; A61B 17/128; A61B 17/1285; A61B 17/083; A61B 17/1222; A61B 17/10
See application file for complete search history.

(56) References Cited

U.S. PATENT DOCUMENTS

| 6,991,634 B2 | 1/2006 | Sugiyama et al. |
| 7,854,739 B2 | 12/2010 | Satake et al. |
| 8,419,751 B2 | 4/2013 | Harada et al. |
| 9,687,248 B2 * | 6/2017 | Satake ................. A61B 17/122 |

(Continued)

FOREIGN PATENT DOCUMENTS

| CN | 109009310 A | 12/2018 |
| JP | 2002-191609 A | 7/2002 |

(Continued)

OTHER PUBLICATIONS

Mark Serisier, "All About Snap Fits in Product Design", Nov. 10, 2017, Dienamics (Year: 2017).*

(Continued)

*Primary Examiner* — Katherine M Rodjom
*Assistant Examiner* — Lindsey R. Rivers
(74) *Attorney, Agent, or Firm* — Morgan, Lewis & Bockius LLP

(57) ABSTRACT

A clip delivery device includes a clip, a first tube configured to store the clip when the clip is closed; a second tube coupled to a proximal end of the first tube; a hook configured to hook a proximal end portion of the clip; a wire coupled to the hook, the wire is configured to pull the hook in a longitudinal direction thereof; an elongated portion coupled to a proximal end of the second tube, the elongated portion having the wire inserted therethrough; and an operating portion coupled to a proximal end of the elongated portion, the operating portion being configured to operate the wire, wherein the hook includes at least one structural mechanism that is configured to suppress rattling that occurs when the proximal end portion of the clip is pulled into the second tube.

20 Claims, 13 Drawing Sheets

(56) References Cited

U.S. PATENT DOCUMENTS

| | | | | |
|---|---|---|---|---|
| 2002/0177861 | A1* | 11/2002 | Sugiyama | A61B 17/122 606/151 |
| 2005/0143767 | A1* | 6/2005 | Kimura | A61B 50/30 606/158 |
| 2006/0259049 | A1 | 11/2006 | Harada et al. | |
| 2008/0027467 | A1 | 1/2008 | Satake et al. | |
| 2008/0140089 | A1 | 6/2008 | Kogiso et al. | |
| 2009/0275958 | A1 | 11/2009 | Harada et al. | |
| 2019/0133597 | A1 | 5/2019 | Osaka et al. | |
| 2020/0205836 | A1 | 7/2020 | Uesaka et al. | |

FOREIGN PATENT DOCUMENTS

| | | |
|---|---|---|
| JP | 2003-000609 A | 1/2003 |
| JP | 2004-121485 A | 4/2004 |
| JP | 4046983 B2 | 2/2008 |
| JP | 4116049 B2 | 7/2008 |
| JP | 4502134 B2 | 7/2010 |
| JP | 6432175 B2 | 12/2018 |
| WO | 2020/122120 A1 | 6/2020 |

OTHER PUBLICATIONS

Office Action dated Nov. 8, 2022, issued in Japanese Patent Application No. 2021-204463.
International Search Report dated Mar. 22, 2022, issued in corresponding Japanese International Patent Application No. PCT/JP2021/047916.

* cited by examiner

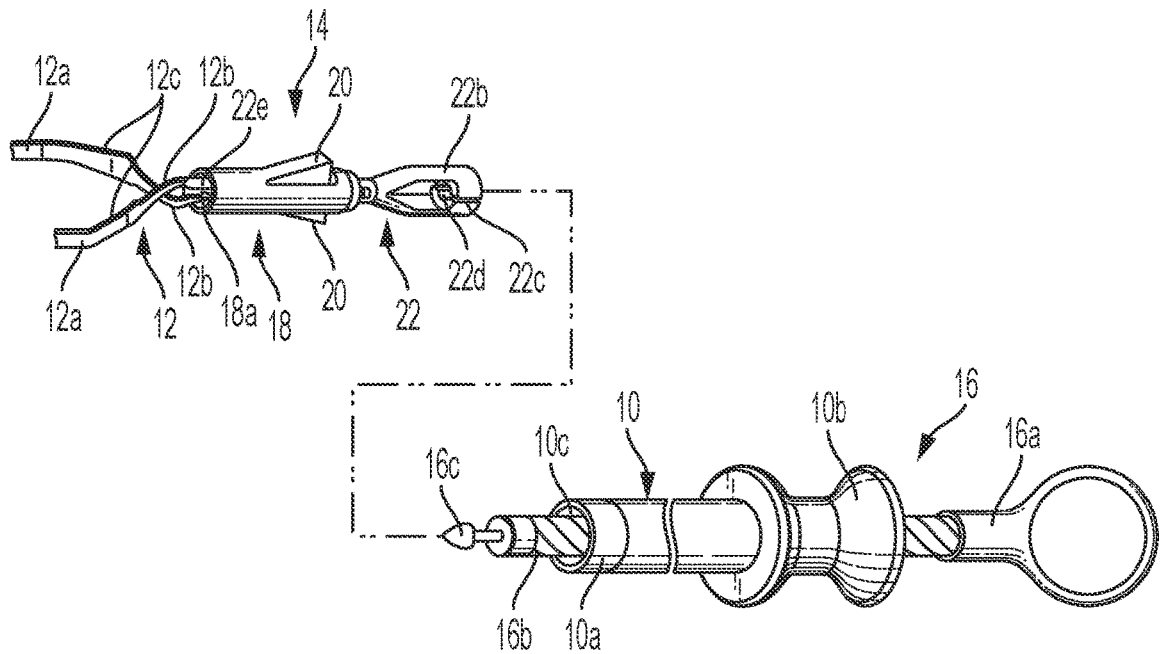
FIG. 1
(PRIOR ART)
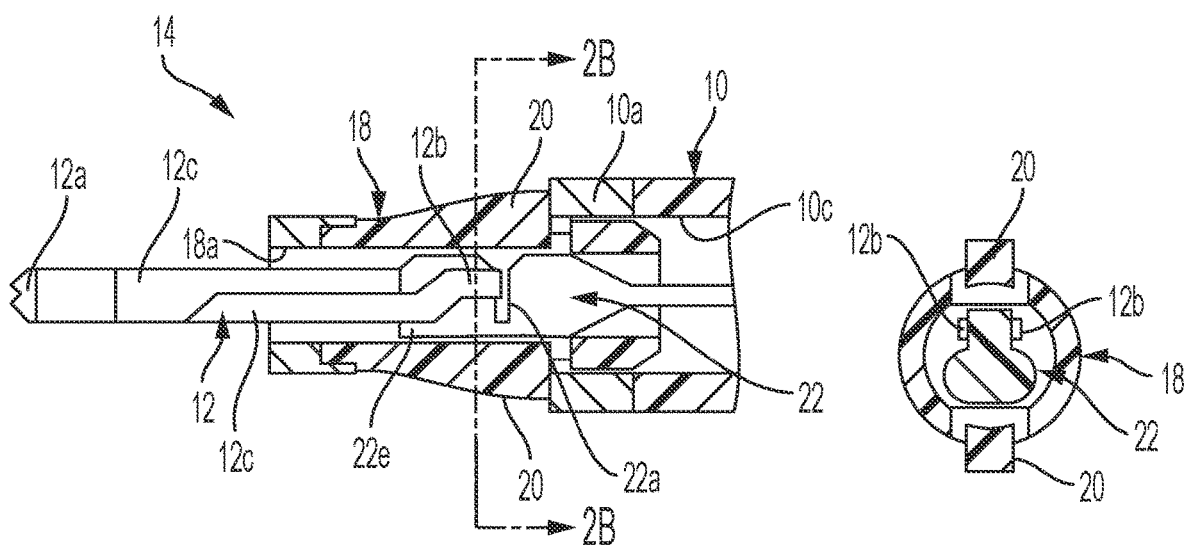
FIG. 2A
(PRIOR ART)
FIG. 2B
(PRIOR ART)

CLIP DELIVERY DEVICE

RELATED APPLICATION DATA

This application is based on and claims priority under 35 U.S.C. § 119 to U.S. Provisional Application No. 63/130,258, filed Dec. 23, 2020, the entire contents of which are incorporated herein by reference.

FIELD OF THE INVENTION

The present invention relates to a clip delivery device and system for ligaturing a living tissue, and more particularly, to a clip delivery device and system associated with an improved clip unit.

DESCRIPTION OF THE RELATED ART

Various clip delivery devices are known. For example, each of Japanese Patent Application Publication Nos. 2002-191609 and 2004-121485 discloses a clip delivery devices for ligaturing tissue. The device comprises an insertion part, which is to be inserted into a forceps channel of an endoscope inserted into a body cavity of a living thing; a clip unit, which includes a clip removably provided at a distal end portion of the insertion part and configured to be opened and closed; and a clip operating part, which includes an external operation portion exposed at a proximal end portion of the insertion part and a clip connecting portion extending from the external operation portion to the distal end portion in the insertion part and connected to the clip unit, and which is configured to open and close the clip of the clip unit by operating the external operating portion.

Such a conventional clip delivery device for ligaturing a living tissue will be explained hereinafter with reference to FIG. 1 to FIG. 6C.

As shown in FIG. 1, a conventional clip delivery device for ligaturing tissue includes an insertion part 10, which is formed with a distal end portion 10a, a proximal end portion 10b, and a passage 10c extending between the distal end portion 10a and the proximal end portion 10b. The insertion part 10 is inserted into a forceps channel or a sheath of an endoscope (not-shown) inserted into a body cavity of a living body with the distal end portion 10a being as a leading end.

The above conventional clip delivery device also includes a clip unit 14. The clip unit 14 includes a clip 12 and the clip unit 14 is removably provided at the distal end portion 10a of the insertion part 10. The clip 12 of the clip unit 14 includes two slender arms 12c having distal ends 12a and proximal end portions 12b connected to each other, and the arms 12c are capable of opening and closing at the distal ends 12a.

The above conventional clip delivery device also includes a clip operating part 16 that is capable of opening and closing the clip 12 of the clip unit 14. The clip operation part 16 includes an external operation portion 16a exposed at the proximal end portion 10b of the insertion part 10 and a clip connecting portion 16b extending in the passage 10c of the insertion part 10 from the external operation portion 16a to the distal end portion 10a of the insertion part 10 and connected to the clip unit 14. The clip 12 of the clip unit 14 can be opened and closed by operating the external operation portion 16a.

Next, a configuration of the conventional clip unit 14 will be explained with reference to FIGS. 1, 2A and 2B. The clip unit 14 comprises a clip holding member 18 whose diameter is smaller than that of an opening of the passage 10c in the distal end portion 10a of the insertion part 10. The clip holding member 18 has a clip projecting/retracting passage 18a which extends along a longitudinal center line of the passage 10c and which holds the clip 12 in a projected/retracted state. When the clip 12 is moved so as to project from and retract into the clip projecting/retracting passage 18a, outside surfaces of the arms 12c of the clip 12 slidingly contact an inner circumferential surface of the clip projecting/retracting passage 18a so that the arms 12c are opened and closed. The clip projecting/retracting passage 18a may be also referred to as a pressing tube or pressing passage which is configured to press the clip unit 14 so as to accommodate the same therein. The clip projecting/retracting passage 18a may include a first tube and a second tube which is connected to the first tube. The second tube is located more proximally than the first tube.

The clip unit 14 further comprises a pair of engaging portions 20 which are provided around the outside surface of the second tube of the clip projecting/retracting passage 18a and which are elastically openable and closable in the radial direction. Each of the engaging portions 20 is slender in a longitudinal direction of the clip projecting/retracting passage 18a. While the clip holding member 18 is retracted in the opening of the passage 10c in the distal end portion 10a of the insertion part 10, each of the engaging portions 20 is pushed by the inner circumferential surface of the passage 10c and elastically bent (that is, closed) about the distal end radially inward relative to the clip projecting/retracting passage 18a. When the clip holding member 18 projects from the opening of the passage 10c, each of the engaging portions 20 elastically expands in the radial direction (that is, opened). The rear ends of the elastically opened engaging portions 20, located opposite to the distal ends in the longitudinal direction of the clip projecting/retracting passage 18a, engage with a periphery of the opening of the passage 10c in the distal end portion 10a of the insertion part 10 in a direction along the longitudinal center line of the passage 10c, and prevent the clip holding member 18 from retracting into the opening of the passage 10c in the distal end portion 10a of the insertion part 10.

The clip unit 14 further comprises a connecting member 22 which is provided in the clip projecting/retracting passage 18a of the clip holding member 18 and which is movable in the extending direction of the clip projecting/retracing passage 18a. The connecting member 22 is connected, at one of its ends, to the proximal end portions 12b of the slender arms 12c of the clip 12 and, at the other of its ends, to the clip connecting portion 16c of the clip operating part 16. The connecting member 22 is operated by the clip operating part 16 to move together with the clip 12 in the above described extending direction in the clip projecting/retracing passage 18a. The connecting member 22 has a breakable portion 22a which can be broken when a pulling force larger than a predetermined value is applied thereto by the clip operating part 16.

In the conventional example shown in FIGS. 1, 2A and 2B, two engaging portions 20 are provided at two positions in the clip holding member 18, the two positions being separated from each other by 180° in a circumferential direction of the clip holding member 18 around the clip projecting/retracting passage 18a. The clip holding member 18 and the two engaging portions 20 are formed as one body by injection molding of synthetic resin with appropriate elasticity and high intensity, such as poly ether ether ketone (PEEK), polyphthalamide (PPA), polyamide (PA), and the like.

The connecting member 22 is formed by injection molding of resin material with high intensity, such as poly ether ether ketone (PEEK), liquid crystal polymer, nylon, and the like. The breakable portion 22a includes a notch or slit, which is cut from a part of an outer circumferential surface of the connecting member 22 inwardly in a radial direction of the clip holding member 18 and which extends in a direction crossing the extending direction of the clip projecting/retracting passage 18a. The proximal end portions 12b connected to each other in the slender arms 12c of the clip 12 are hooked into this notch or slit.

A proximal end portion 22b of the connecting member 22 is branched into two sections, the proximal end portion 22b being closer to the distal end portion 10a of the insertion part 10 than the breakable portion 22a. Two branched sections are close to each other with a longitudinally extending division line 22c interposed therebetween, and a connection hole 22d extending along the longitudinal center line of the clip projecting/retracting passage 18a is formed in closely facing ends of the branched sections. In the connection hole 22d at the two branched sections of the proximal end portion 22b of the connecting member 22, a substantially conically shaped engaging portion 16c of a projecting end of a projection projecting from the distal end of the clip connecting portion 16b of the clip operating part 16 in the longitudinal direction of the clip operating part 16 is pressed in, so that a rotational connection between the two branched sections of the proximal end portion 22b of the connecting member 22 and the clip connecting portion 16b of the clip operating part 16 is achieved.

A part of the outer circumferential surface of the connecting member 22 is flattened, and a part of the inner circumferential surface of the clip projecting/retracting passage 18a of the clip holding member 18, the part corresponding to the flattened part of the outer circumferential surface of the connecting member 22, is also flattened. The flattened part of the inner circumferential surface of the clip projecting/retracing passage 18a extends in a moving range of the flattened part of the outer circumferential surface of the connecting member 22 while the connecting member 22 moves in the clip projecting/retracting passage 18a. As a result, as shown in FIG. 2B, the connecting member 22 does not rotate in the circumferential direction within the clip projecting/retracting passage 18a.

A moving path of the breakable part 22a of the connecting member 22 in the clip projecting/extracting passage 18a is adjacent to the inside surface of one of the two engaging portions 20.

Next, a process of ligaturing a desired region of a desired tissue in a body cavity of a living thing, for example a human body, by using the conventional clip delivery device configured as described above will be explained with reference to FIGS. 3A-3D.

First, the insertion part 10 of the endoscope is inserted into the body cavity, and the distal end of the insertion tube is directed to the desired region of the desired tissue. Then, the insertion part 10 of the conventional clip delivery device is inserted into the forceps channel or the sheath of the endoscope with the distal end portion 10a being as the leading end. At this time, the clip 12 is retracted into the clip projecting/retracting passage 18a of the clip holding member 18, and the clip holding member 18 is retracted into the distal end portion of the passage 10c of the insertion part 10.

After the distal end portion 10a of the insertion part 10 is projected from the distal end opening of the forceps channel of the insertion part of the endoscope, the external operation portion 16a of the clip operating part 16 is pushed to project the clip holding member 18 from the distal end portion of the passage 10c of the insertion part 10 and to project the clip 12 from the clip projecting/retracing passage 18a of the clip holding member 18. Each of the two engaging portions 20 of the projected clip holding member 18 is elastically expanded (that is, opened) around its distal end outward in the radial direction of the clip holding member 18, as shown in FIG. 3A. The rear ends of the opened engaging portions 20 are engaged with the periphery of the opening of the passage 10c in the distal end portion 10a of the insertion part 10 in the direction along the longitudinal center line of the passage 10c, and prevent the clip holding member 18 from retracting into the opening of the passage 10c in the distal end portion 10a of the insertion part 10.

As shown in FIG. 3A, as the connecting member 22 moves forward (in direction indicated by arrow F) the distal ends 12a of the arms 12c of the clip 12 open outward in the radial direction. The gap between the opened distal ends 12a of the arms 12c of the clip 12 are then located on the desired region DR of the desired tissue in the body cavity of the living thing, for example the human body. Then, to close the opened distal ends 12a of the arms 12c of the clip 12 on the desired region DR of the desired tissue, the external operation portion 16a is manipulated to move the connecting member 22 in direction indicated by arrow R. As a result, while the arms 12c of the clip 12 are pulled into the clip projecting/retracting passage 18a of the clip holding member 18, the outside surfaces of the arms 12c slidingly contact the periphery of the opening of the clip projecting/retracing passage 18a at the projecting end of the clip holding member 18 and are pushed inward in the radial direction, so that the distal ends 12a of the arms 12c of the clip 12 can hold the desired region DR of the desired tissue, as shown in FIG. 3B.

By further pulling the external operation portion 16a, a pulling resistance generated in the desired region DR of the desired tissue and a frictional resistance generated on the outside surface of the arms 12c of the clip 12 with respect to the periphery of the opening of the clip projecting/retracing passage 18a are increased. Further increasing of these forces applied to the base of the breakable portion 22a of the connecting member 22 results, once the forces are at a predetermined value, in propagation of the notch/slit to separate the distal end portion 22e from the base.

In a case that the opening distance of the distal ends 12a of the arms 12c of the clip 12 is relative large when the opened distal ends 12a of the arms 12c of the clip 12 bites the desired region DR of the desired tissue as shown in FIG. 3B, the deviating force BF around the base of the breakable portion 22a is applied to the distal end portion 22e of the connecting member 22 as shown in FIG. 3C before the arms 12c of the clip 12 are sufficiently pulled into the clip projecting/retracting passage 18a of the clip holding member 18. At this time, the distal end portion 22e of the connecting member 22 faces the inside surface of one of the two engaging portions 20 of the clip holding member 18 in the clip projecting/retracing passage 18a. Therefore, the distal end portion 22e of the connecting member 22 to which the deviating force BF is applied pushes the inside surface of the engaging portion 20 corresponding to the distal end portion 22e of the connecting member 22 outward in the radial direction of the clip projecting/retracting passage 18a, until the base of the breakable portion 22a of the connecting member 22 is broken as shown in FIG. 3D.

Due to the deviating force BF, the arms 12c of the clip 12 are prevented from being pulled furthermore into the clip projecting/retracting passage 18a of the clip holding member 18, and consequently, the bite of the distal ends 12a of the arms 12 of the clip 12 in the desired region DR of the desired tissue (namely, the ligaturing of the desired region DR of the desired tissue) may be insufficient for a desired procedure.

In addition to the conventional clip apparatus described above with reference to FIGS. 1 to 3D, another conventional clip apparatus is also known as shown in FIG. 4 to FIG. 6C. This conventional clip apparatus is different from the above described conventional clip apparatus in that a ring portion 32 and a helical spring 36 are provided in the clip unit 14.

As shown in FIG. 4, the locking ring portion 32 is arranged at a proximal end of the clip projecting/retracting passage 18a, and is also located more proximally than the engaging portion 20. The locking ring portion 32 has an inner diameter that is smaller than an inner diameter of the clip projecting/retracting passage 18a.

As shown in FIG. 6B, from the inner circumferential surface of the proximal end of the clip projecting/retracting passage 18a, the locking ring portion 32 protrudes over the entire inner circumference surface. An inner surface 32a of the locking ring portion 32 is formed in a circular shape that is coaxial with the clip projecting/retracting passage 18a.

The locking ring portion 32 may be formed of a material such as, for example, a stainless steel (SUS304), a titanium alloy (Ti-6AL-4V) or a cobalt-chromium alloy. More preferably, the surface hardness is increased by nitriding SUS304.

Referring to FIG. 4, the helical spring 36 is accommodated inside the clip projecting/retracting passage 18a. An end turn portion 36b is provided at the distal end of the helical spring 36. The inner diameter of the formed end turn portion 36b is less than that of the other portions of the helical spring 36.

As shown in FIG. 5, when the helical spring 36 is accommodated inside the clip projecting/retracting passage 18a, the distal end 36b of the helical spring 36 is attached to protrusion portions 23 and 24 formed on the clip arms 12c and the proximal end 36a of the helical spring 36 is attached to the proximal end of the locking ring portion 32 as shown in FIG. 6B.

The protrusion portions 23 and 24 interlock with the end turn portion 36b of the helical spring 36. Even when the helical spring 36 does not include the end turn portion 36b, a separate member such as a washer at the distal end of the helical spring 36 may be used.

As shown in FIGS. 4 and 5, the proximal ends of the arms 12c are located distally with respect to the locking ring portion 32 inside the clip projecting/retracting passage 18a. In the state shown in FIG. 5, locked portions 25 and 26 do not come into contact with the locking ring portion 32, and the distal ends of the arms 12c of the clip 12 are separated from each other so as to be in an opened state.

FIGS. 6A and 6B show a state in which the clip 12 and the connecting member 22 are pulled into a position at which the breakable portion is to be broken. As shown in FIGS. 6A and 6B, in order for the connecting member 22 to be advanced and retracted through the dip projecting/retracting passage 18a, an outer diameter of the connecting member 22 has to be smaller than an inner diameter of the clip projecting/retracting passage 18a. Further, in order for the connecting member 22 to pass through the locking ring portion 32, which has an inner diameter smaller than the inner diameter of the engaging portion 20, the outer diameter of the connecting member 22 cannot be larger than an inner diameter of the locking ring portion 32. Thus, for this structural reason, as shown in FIG. 6B, a gap G1 exists between the outer diameter of the connecting member 22 and the inner diameter of the engaging portion 20. Due to the gap G1, relative motion between the clip 12 and the connecting member 22 can occur, for example due to rattling when they are pulled or pushed by the external operating portion 16a. The relative motion can cause the clip to come off the connecting member 22, e.g., proximal end portions 12b of the clip 12 can move out of the slot of the breakable portion 22a.

Further, as shown FIG. 6C, when the connecting member 22 is pulled by the external operation portion 16a to pass through the locking ring portion 32, a pulling force is high enough to move the locked portions 25 and 26 proximally beyond the locking ring portion 32. Also, by further pulling the connecting member 22, a pulling resistance generated in the desired region DR of the desired tissue and a resistance generated by the helical spring 36 are increased. Further increasing of these forces applied to the base of the breakable portion 22a of the connecting member 22 results, once the forces are at a predetermined value, in propagation of the notch/slit to separate the distal end portion 22e from the base.

However, as shown in FIG. 6C, a bending moment M around the base of the breakable portion 22a is applied to the distal end portion 22e of the connecting member 22, thereby causing the distal end portion 22e to move in a radial direction and expanding the effective diameter of the connecting member 22. In this situation, a gap G2 between the base of the breakable portion 22a and a center of load received from the proximal end portions 12b of the clip 12 increases, which causes an outer surface of the connecting member 22 to contact an inner surface of the engaging portion 20. The bending moment M negatively affects the longitudinal movement of the clip 12 and the connecting member 22, thereby decreasing the force available to successfully break the breakable portion 22a.

SUMMARY OF THE INVENTION

Accordingly, the present disclosure is directed to a clip delivery device and clip unit, which substantially obviate one or more of the issues due to limitations and disadvantages of related clip delivery device and system.

An object of the present disclosure is to provide a clip delivery device for ligaturing a living tissue, comprising an elongated insertion part which can be inserted into a body cavity of the living tissue along a longitudinal direction thereof; a clip unit which includes a clip having arms capable of elastically opening and closing distal end portions thereof around mutually connected proximal ends thereof, and which can be projected from and retracted into the insertion part through an opening at a distal end portion of the insertion part; and a clip operating part which extends in the insertion part, which includes an external operation portion exposed at a proximal end portion of the insertion part and a clip connecting portion connected to the clip unit, and which operates the projection and retraction of the clip by the external operation portion. The clip unit includes a clip passage in which the clip is housed to project from and to be retracted into the clip passage so that the arms of the clip open and close the distal end portions thereof elastically; a connecting member which is movably housed in the clip passage, which has a distal end portion, a proximal end portion, and a breakable portion between the distal end portion and the proximal end portion, the distal end portion being connected to the proximal ends of the clip, the proximal end portion being connected to the clip connecting portion of the clip operating part. The clip unit further includes at least one snap-fit member by which the clip and the connecting member engage with each other.

Another object of the present disclosure is to provide a clip delivery device for ligaturing a living tissue, comprising: an elongated insertion part which can be inserted into a body cavity of the living tissue along a longitudinal direction thereof; a clip unit which includes a clip having arms capable of elastically opening and closing distal end portions thereof around mutually connected proximal ends thereof, and which can be projected from and retracted into the insertion part through an opening at a distal end portion of the insertion part; and a clip operating part which extends in the insertion part, which includes an external operation portion exposed at a proximal end portion of the insertion part and a clip connecting portion connected to the clip unit, and which operates the projection and retraction of the clip by the external operation portion. The clip unit includes a clip passage in which the clip is housed to project from and to be retracted into the clip passage so that the arms of the clip open and close the distal end portions thereof elastically, a locked portion which protrudes from the proximal ends of the arms, a locking ring portion which protrudes from an inner circumferential surface of a proximal end of the clip passage; a connecting member which is movably housed in the clip passage, which has a distal end portion, a proximal end portion, and a breakable portion between the distal end portion and the proximal end portion, the distal end portion being connected to the proximal ends of the clip, the proximal end portion being connected to the clip connecting portion of the clip operating part. The distal end portion of the connecting member includes an extended body which extends in the longitudinal direction toward the distal ends of the arms, and the locking ring portion is located more proximally than the extended body of the distal end portion of the connecting member.

Still another object of the present disclosure is to provide a clip unit for ligaturing a living tissue, comprising a clip having arms capable of elastically opening and closing distal end portions thereof around mutually connected proximal ends thereof, a clip passage in which the clip is housed to project from and to be retracted into the clip passage so that the arms of the clip open and close the distal end portions thereof elastically; a connecting member which is movably housed in the clip passage, which has a distal end portion, a proximal end portion, and a breakable portion between the distal end portion and the proximal end portion, the distal end portion being connected to the proximal ends of the clip, wherein the clip unit further includes at least one snap-fit member by which the clip and the connecting member engage with each other.

Still another object of the present disclosure is to provide a clip unit for ligaturing a living tissue, comprising a clip having arms capable of elastically opening and closing distal end portions thereof around mutually connected proximal ends thereof, a clip passage in which the clip is housed to project from and to be retracted into the clip passage so that the arms of the clip open and close the distal end portions thereof elastically, a locked portion which protrudes from the proximal ends of the arms, a locking ring portion which protrudes from an inner circumferential surface of a proximal end of the clip passage; a connecting member which is movably housed in the clip passage of the clip holding member, which has a distal end portion, a proximal end portion, and a breakable portion between the distal end portion and the proximal end portion, the distal end portion being connected to the proximal ends of the clip. The distal end portion of the connecting member includes an extended body which extends in the longitudinal direction toward the distal ends of the arms, and the locked portion is located more proximally than the extended body of the distal end portion of the connecting member.

Additional features and advantages will be set forth in the description that follows, and in part will be apparent from the description, or may be learned by practice of the invention. The objectives and other advantages of the disclosed clip delivery device and system will be realized and attained by the structure particularly pointed out in the written description and claims thereof as well as the appended drawings.

BRIEF DESCRIPTION OF THE DRAWING

The following detailed description of preferred embodiments can be read in connection with the accompanying drawings in which like numerals designate like elements and in which:

FIG. 1 is a perspective view schematically showing a conventional clip delivery device and system for ligaturing a living tissue.

FIG. 2A is an enlarged longitudinal sectional view schematically showing a clip unit in the conventional clip delivery device and system for ligaturing a living tissue shown in FIG. 1, and FIG. 2B schematically shows a transverse sectional view taken along a line IIB-IIB in FIG. 2A.

Figure 3A:
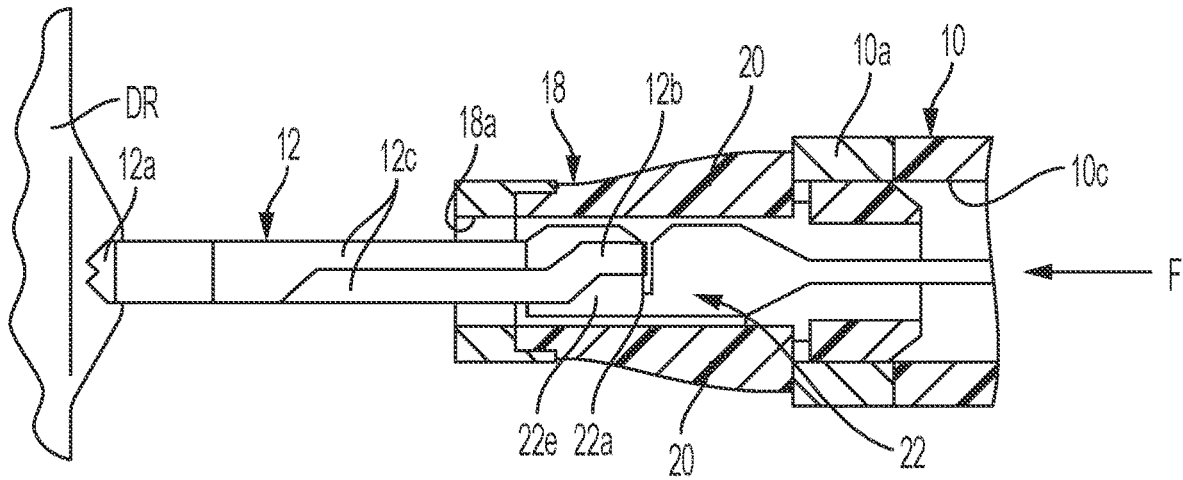
FIGS. 3A, 3B, 3C and 3D are longitudinal sectional views schematically showing sequential configurations of the clip unit in the clip delivery device of FIGS. 2A and 2B during an operation for ligaturing a desired region of a desired tissue in a body cavity of a living thing.
Figure 3B:
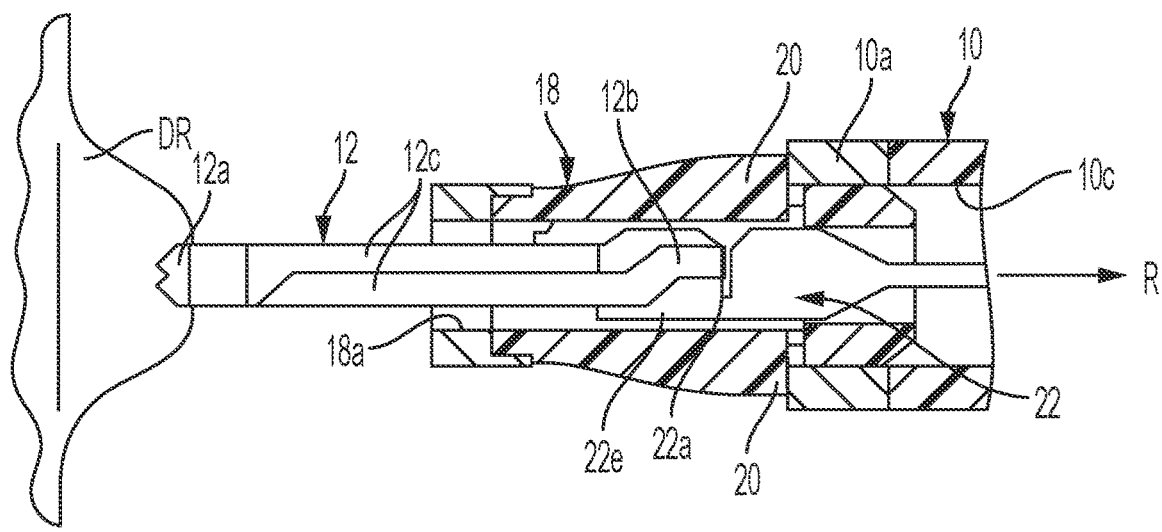
Figure 3C:
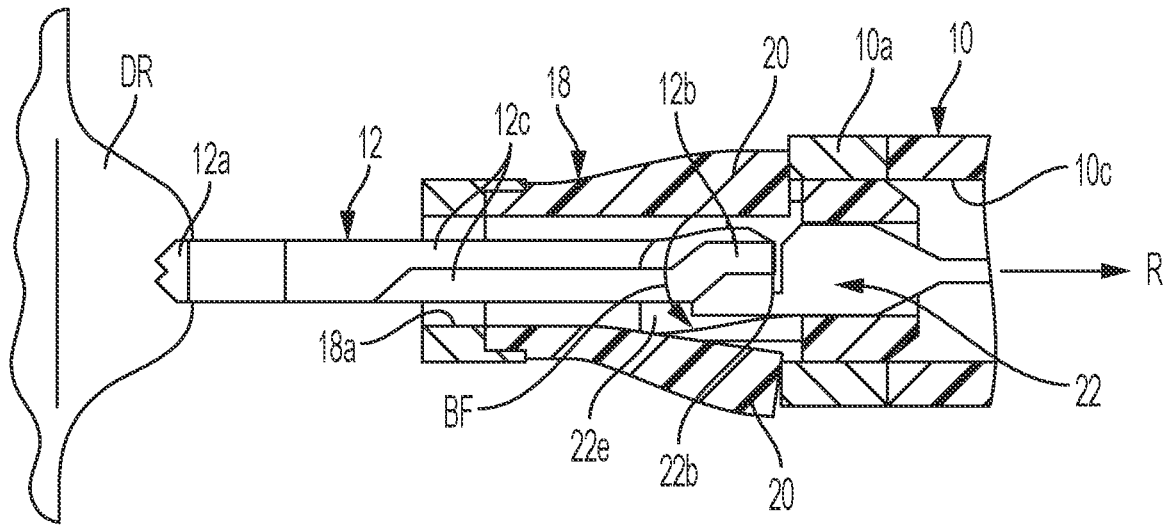
Figure 3D:
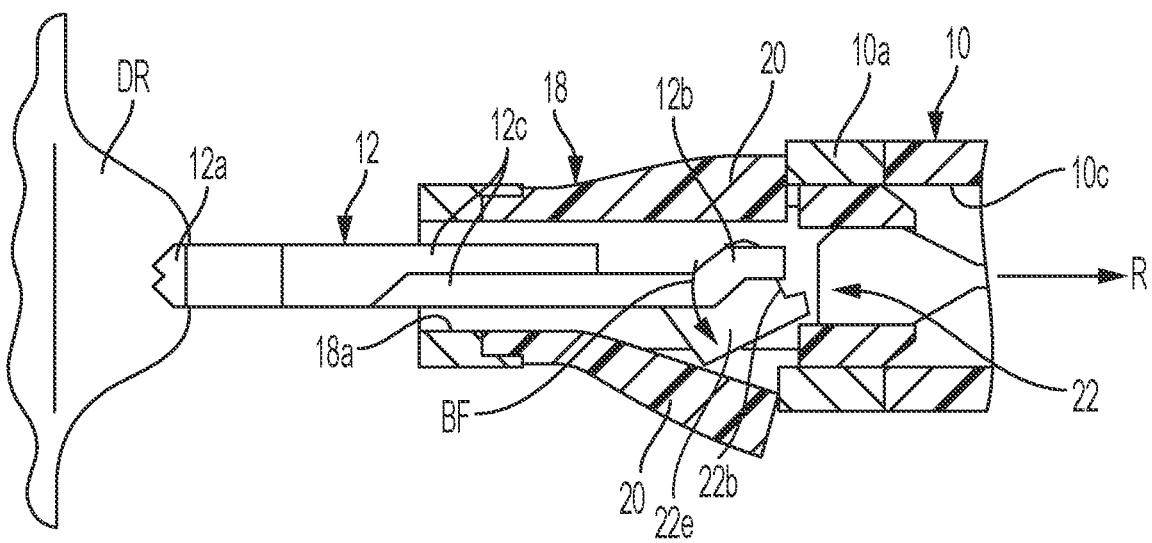
Figure 4:
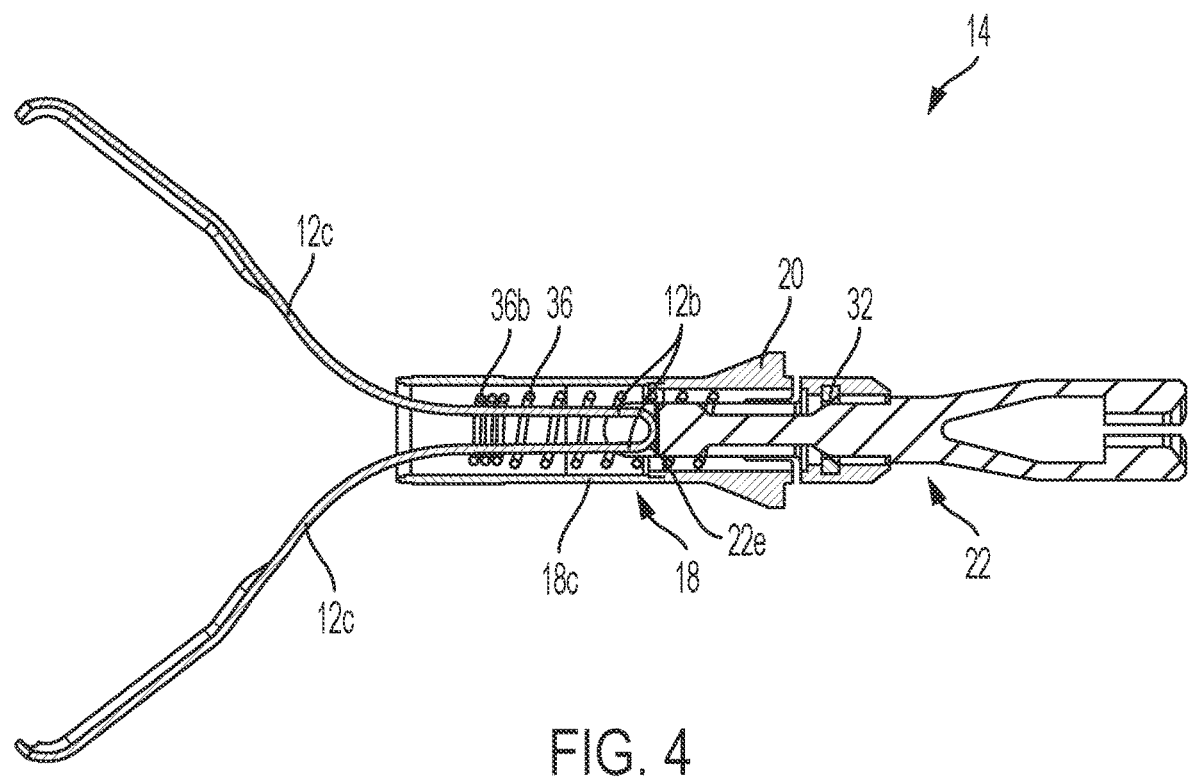
FIG. 4 is a sectional top view schematically showing another conventional clip delivery device and system for ligaturing a living tissue.
Figure 5:
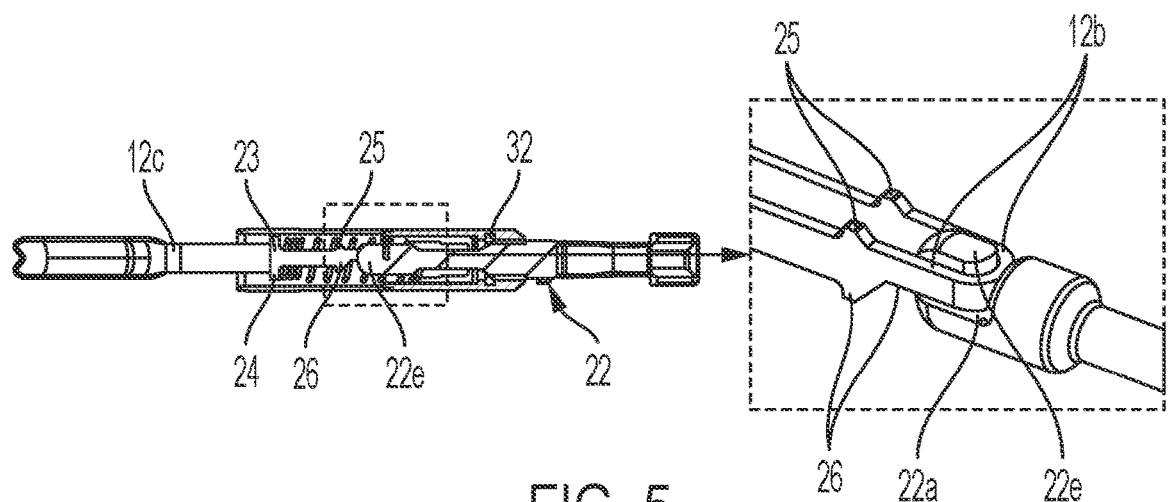
FIG. 5 is a sectional side view schematically showing the conventional clip delivery device and system of FIG. 4, with an enlarged view schematically showing connection between a clip and a connecting member.

For ease of viewing, in some instances only some of the named features in the figures are labeled with reference numerals.

DETAILED DESCRIPTION

Hereinafter, accompanying drawings, which are incorporated in and constitute a part of the specification, illustrate embodiments of the invention, and together with the general description given above and the detailed description of the embodiments given below, serve to explain the principles of the invention. Throughout all of the drawings, ratios of the thicknesses or dimensions of respective constituent elements are appropriately adjusted for clarity.

Also, it should be noted that references throughout this disclosure to the terms "distal" and "distally" are to a direction away from the clip operating part 16 (see FIG. 1), while references to the terms "proximal" and "proximally" are to a direction towards the clip operating part 16.

First Embodiment

Figure 7A:
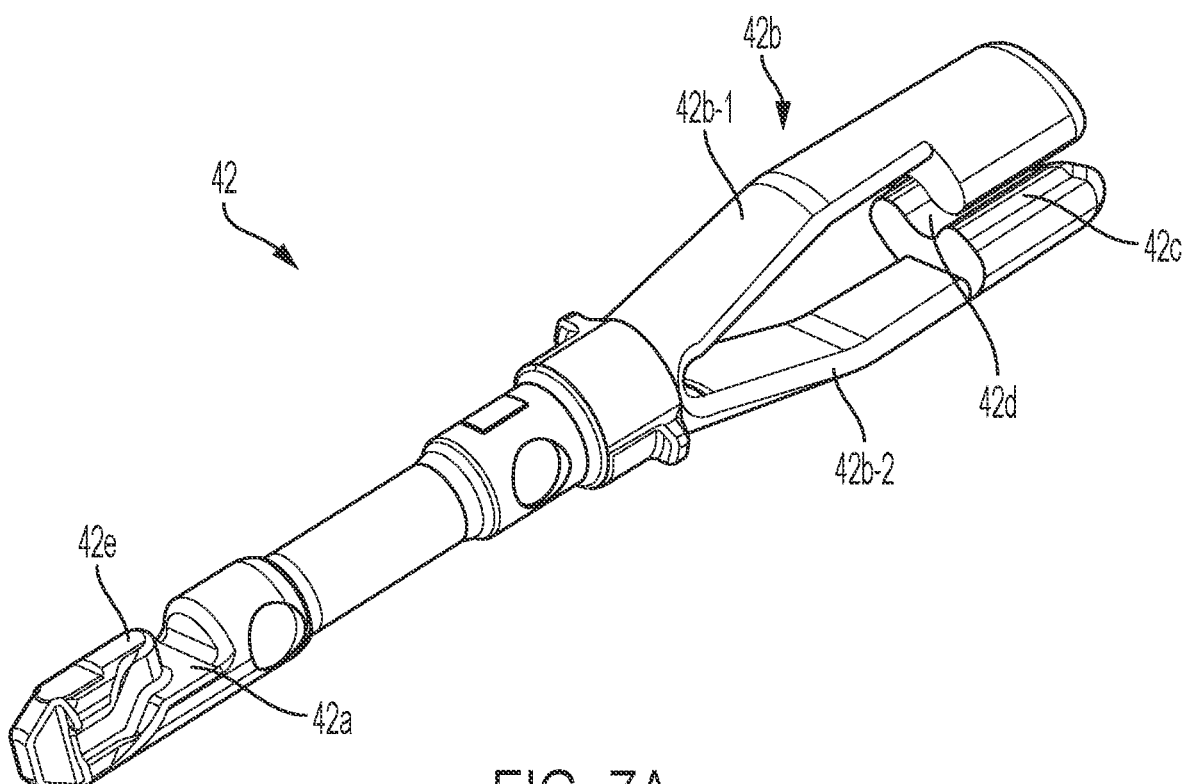
FIG. 7A is a perspective view schematically showing a connecting member of a clip unit associated with a clip delivery device according to a first exemplary embodiment.
Figure 7B:
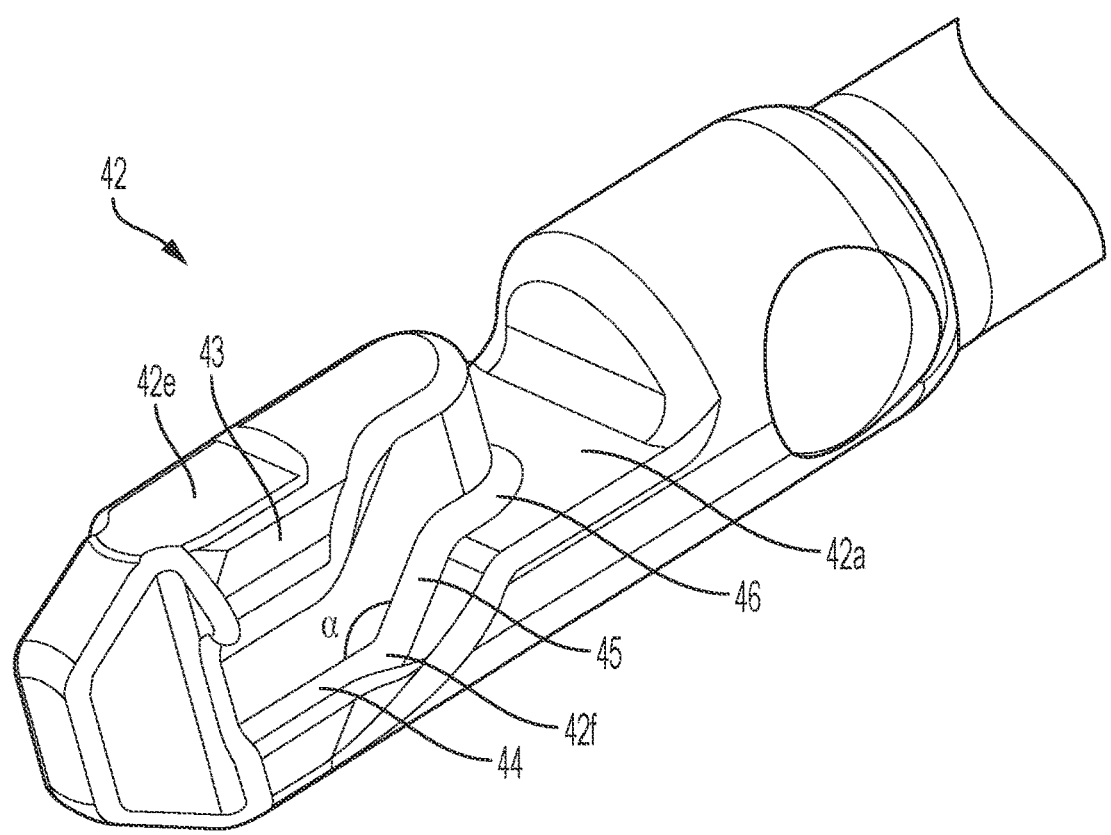
FIG. 7B is an enlarged view schematically showing a snap-fit structure according to the first exemplary embodiment.

FIG. 7A is a prospective view schematically showing a snap-fit type clip unit of a clip delivery device according to a first exemplary embodiment, and FIG. 7B is an enlarged view schematically showing a snap-fit mechanism of the connecting member of FIG. 7A according to the exemplary embodiment. The clip delivery device according to the first exemplary embodiment is different from conventional clip delivery devices in that a clip unit has a different configuration.

The clip unit of this exemplary embodiment is a snap-fit type clip unit, in which a snap-fit member may be attached to a clip or to a connecting member. The snap-fit member is configured to control and stabilize the connection between the clip and the connecting member, so as to achieve a smooth and stable operation of the clip unit along a moving path in the direction of a longitudinal axial line of a clip projecting/retracting passage. The snap-fit member is able to suppress the rattling therebetween and associated relative motion that can occur during the projecting and retracting of the clip and the connecting member inside the clip projecting/retracting passage, and also able to minimize the deviation force and/or the bending moment generated during the operation of the clip unit as described above, and therefore a breaking force can be successfully applied to a breakable portion of the connecting member, which is required by the clip-delivering operation.

As shown in FIG. 7A, in this exemplary embodiment, a connecting member 42 is configured to be disposed inside the clip holding member 18 and be movable in the extending direction of the clip holding member 18. The connecting member 42 includes a proximal end portion 42b that is connected to the clip connecting portion 16b of the clip operating part 16, and a distal end portion 42e has surfaces forming a hook, by which the proximal end portions 12b of the slender arms 12c of the clip 12 are hooked on the connecting member 42.

The connecting member 42 is operated by the clip operating part 16 to project and retract together with the clip 12 inside the clip projecting/retracing passage 18a along a longitudinal direction thereof. The connecting member 42 includes a breakable portion 42a which is broken when a pulling force larger than a predetermined value is applied thereto by the clip operating part 16. The breakable portion 42a has a reduced cross-sectional area (relative to other portions of the connecting member, particularly those portions closer to the proximal end portion 42b) to preferential break at this location.

Figure 8A:
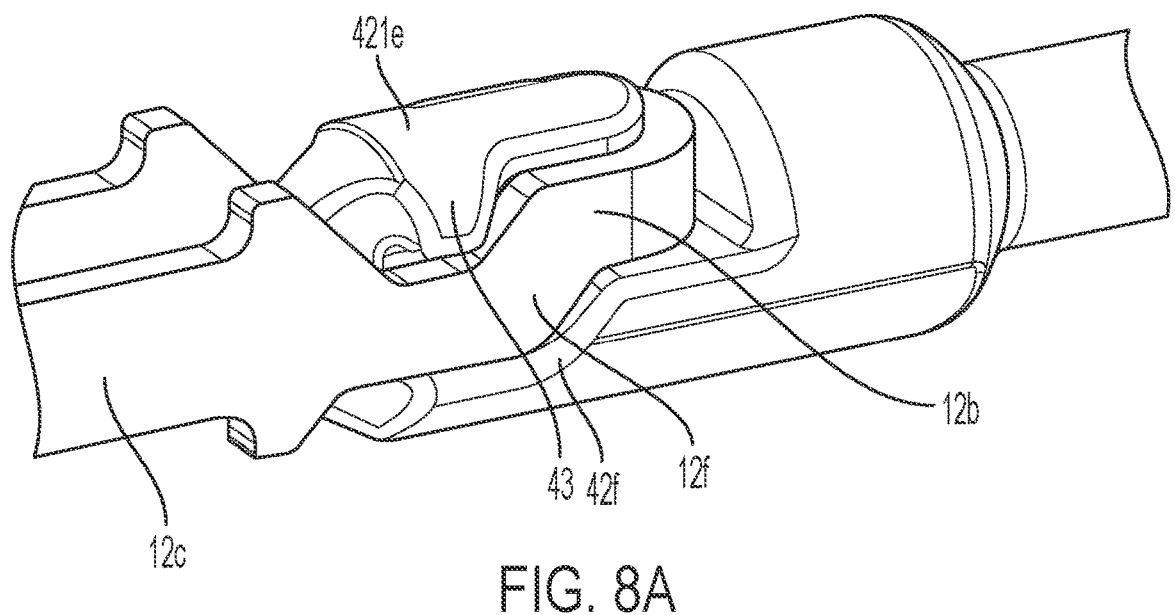
FIGS. 8A-8D are different schematic views illustrating the snap-fit structure in which a a clip and a connecting member are engaged with each other according to the first exemplary embodiment.
Figure 8B:
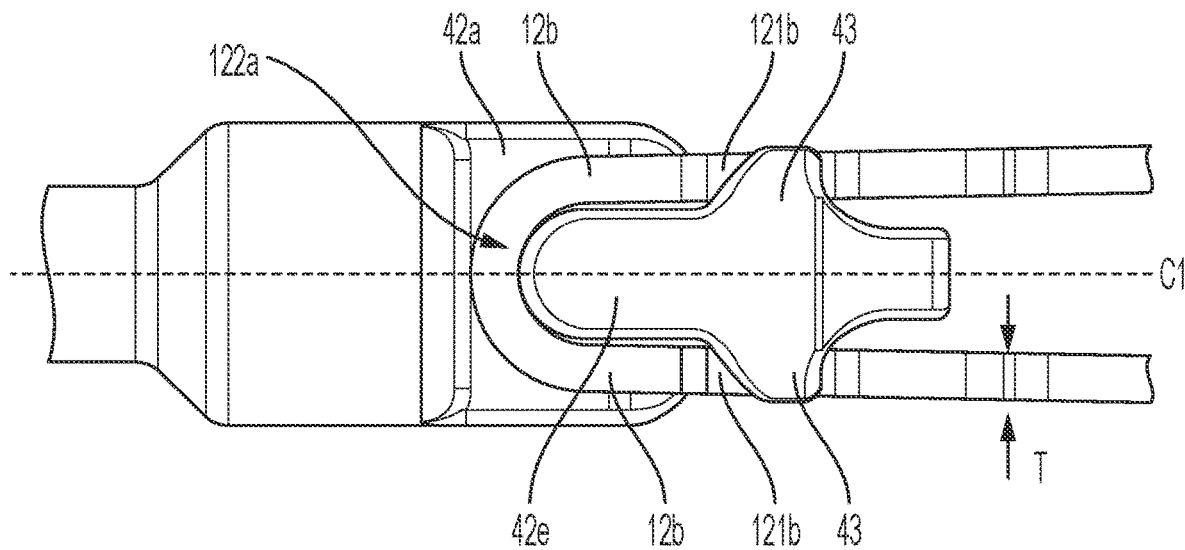

The connecting member 42 may be formed by injection molding of resin material with high intensity, such as poly ether ether ketone (PEEK), liquid crystal polymer, nylon, and the like. The breakable portion 42a may be a notch or slit which is cut from a part of an inner circumferential surface of the connecting member 42 outwardly in a radial direction of the clip holding member 18 and which extends in a direction crossing the longitudinal direction (or an extending direction) of the clip projecting/retracting passage 18a. In this notch or slit, as shown in FIG. 8B, the proximal end portions 12b, which are connected to each other in the slender arms 12c of the clip 12, are hooked at the breakable portion 42a by the distal end portion 42e of the connecting member 42.

As shown in FIG. 7B, the connecting member 42 further includes a plurality of seating surfaces 44, 45 and 46, which are formed to receive bottom (lateral) surfaces 122b (in FIG. 8D) of the proximal end portions 12b of the clip 12. The seating surfaces 44, 45, and 46 are shaped to be in conformity with the configuration of the proximal end portions 12b, which includes a stepped portion 12f as shown in FIG. 8A. The seating surfaces 44, 45 and 46 are each formed to have a width that is equal to or greater than the thickness (T in FIG. 8B) of the proximal end portions 12b. The seating surfaces 44 and 45 form a stepped portion 42f corresponding to the stepped portion 12f of the proximal end portions 12b. The seating surface 46 is formed on the base of the breakable portion 42a around the hook (the distal end portion 42e). The stepped portion 42f has an angle α at the bottom of distal end portion 42e. The invention is not limited to the angle disclosed in this exemplary embodiment, and any suitable angle for the stepped portion 42f can be used, from greater than 90 degrees to 180 degrees. The sum of the angle α and an angle θ (in FIG. 8C) is 180 degrees or less. In exemplary embodiments, the angle α and an angle θ have the same value, i.e., stepped portion 42f of the seating surfaces is parallel to the complementary stepped portion 431 of the snap-fit member 43.

A proximal end portion 42b of the connecting member 42 may be branched into two sections, the proximal end portion 42b being closer to the distal end portion 10a of the insertion part 10 than the breakable portion 42a. Two branched sections 42b-1 and 42b-2 are close to each other with a longitudinally extending division line 42c interposed therebetween, and a connection hole 42d extending along a longitudinal center line of the clip projecting/retracting passage 18a is formed in closely facing ends of the branched sections. In the connection hole 42d at the two branched sections of the proximal end portion 42b of the connecting member 42, a substantially conically shaped engaging portion 16c of a projecting end of a projection projecting from the distal end of the clip connecting portion 16b of the clip operating part 16 in the longitudinal direction of the clip operating part 16 is pressed in, so that a rotational connection between the two branched sections of the proximal end portion 42b of the connecting member 42 and the clip connecting portion 16b of the clip operating part 16 is achieved.

A part of the outer circumferential surface of the connecting member 42 may be flattened, and a part of the inner circumferential surface of the clip projecting/retracting passage 18a of the clip holding member 18, which corresponds to the flattened part of the outer circumferential surface of the connecting member 42, may be also flattened. The flattened part of the inner circumferential surface of the clip projecting/retracing passage 18a extends in a moving range of the flattened part of the outer circumferential surface of the connecting member 42 while the connecting member 42 moves in the clip projecting/retracting passage 18a.

Figure 6A:
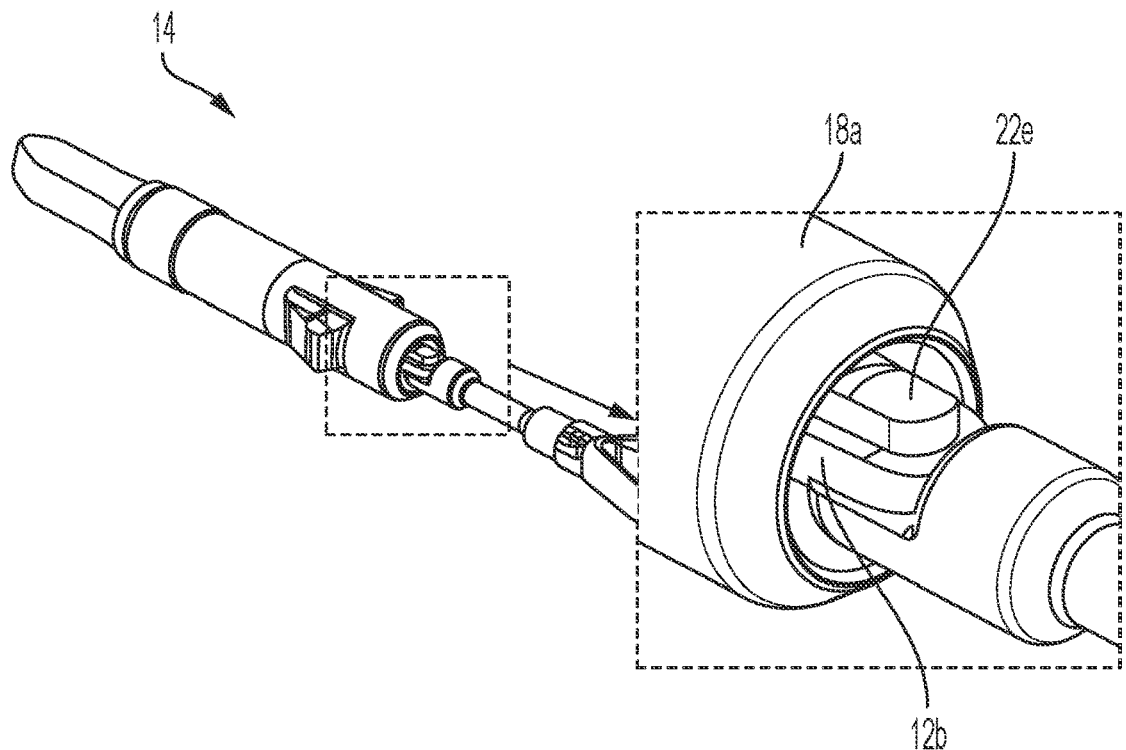
FIG. 6A is a perspective view schematically showing a clip unit of the clip delivery device of FIG. 4 in a state in which a clip and a connecting member are pulled to a breakable position.
Figure 6B:
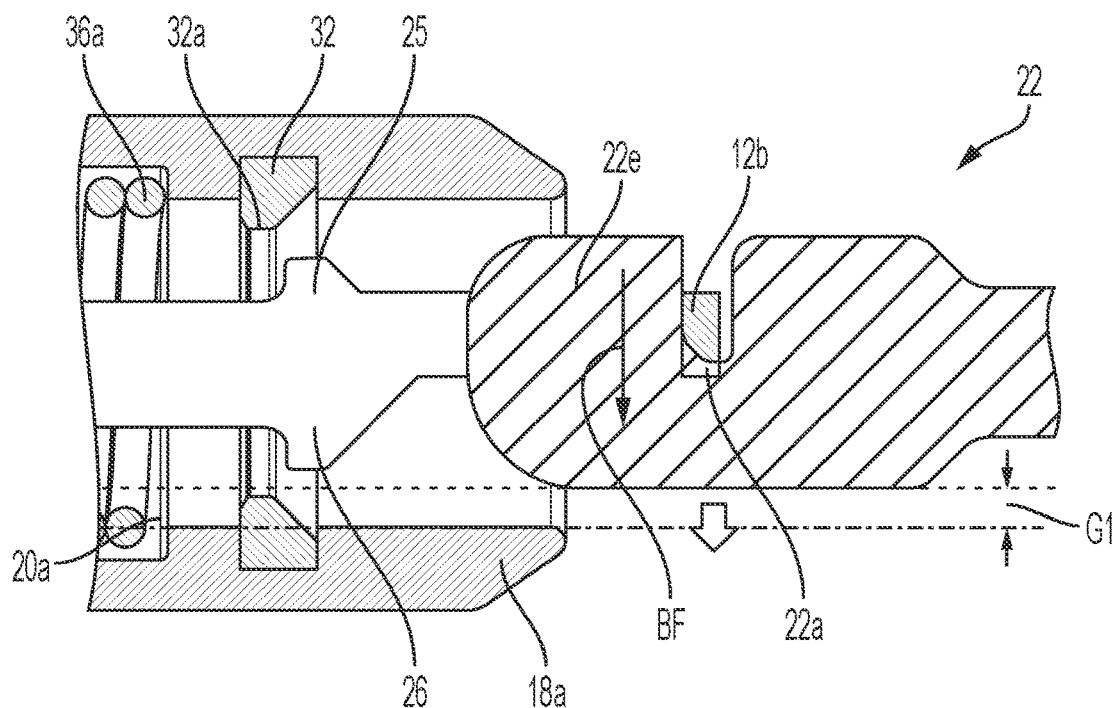
FIG. 6B is a sectional view schematically showing one disadvantage situation of the clip delivery device of FIG. 4.

A moving path of the clip 12 and the connecting member 42 inside the clip holding member 18 is adjacent to an inner surface of the clip holding member 18. In other words, a space (like the gap G1 as shown in FIG. 6B) exists between the outer surface of the connecting member 42 and the inner surface of the clip holding member 18. When the clip 12 and the connecting member 42 on which the clip 12 is hooked by the distal end portion 42e are advanced and retracted inside the clip holding member 18 by the external operation portion 16a, rattling and associated relative motion occurs between the clip 12 and the connecting member 42, and a deviating force BF generated by the rattling is applied around the base of the breakable portion 42a in a diameter expansion direction of the connecting member 42. Due to the deviating force BF, the proximal end portions 12b of the clip 12 becomes easily coming off the distal end portion 42e (the hook) of the connecting member 42. Also, the deviating force BF conflicts with the longitudinal movement of the connecting member 42, thereby decreasing a pulling force that is necessary to successfully breaking the breakable portion 42a.

Figure 6C:
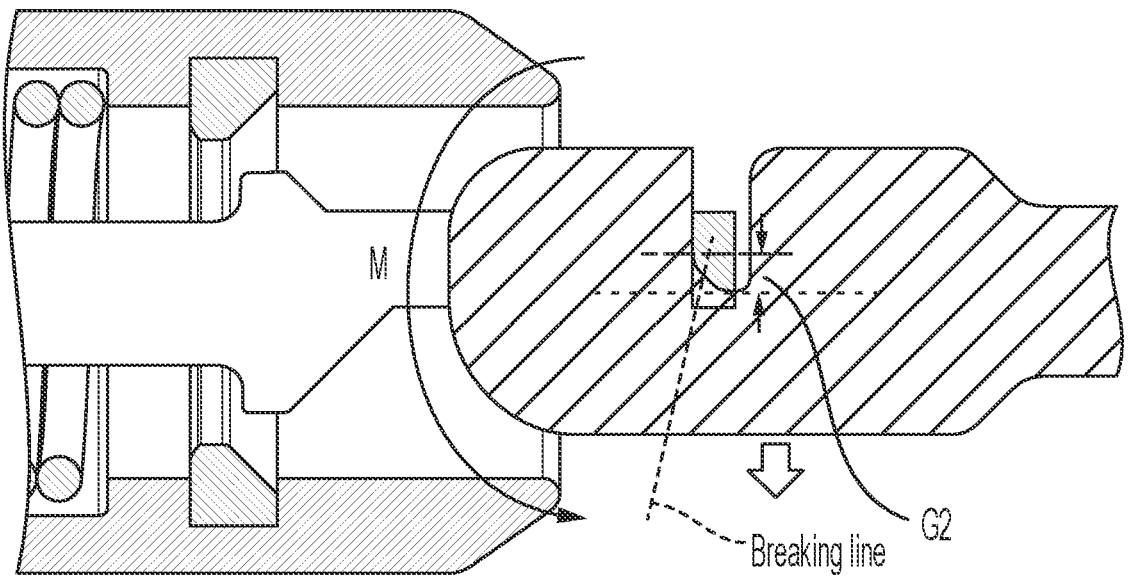
FIG. 6C is a sectional view schematically showing another disadvantage situation of the clip delivery device of FIG. 4.

Also, by pulling the clip and the connecting member 42 by the external operating part 16, a bending moment M around the base of the breakable portion 42a is applied to the distal end portion 42e of the connecting member 42, thereby causing the distal end portion 42e to move in a diameter expansion direction of the connecting member 42. In this situation, a gap (like the gap G2 in FIG. 6C) between the base of the breakable portion 42a and a center of load received from the proximal end portions 12b of the clip 12 increases, which causes an outer surface of the connecting member 42 to contact an inner surface of the clip projecting/retracting passage 18a. The bending moment M negatively affects the longitudinal movement of the clip 12 and the connecting member 42, thereby decreasing the force of successfully breaking the breakable portion 42a.

In order to prevent the proximal end portions 12b of the clip 12 from coming off the distal end portion 42e (the hook) of the connecting member 42 and to effectively control (resist) the deviating force BF and the bending moment M, the connecting member 42 further includes a snap-fit mechanism.

As shown in, for example, FIGS. 8A-8D, the snap-fit mechanism is formed on the connecting member 42. In this exemplary embodiment, the snap-fit mechanism includes a pair of snap-fit members 43 projecting from two sides of a top surface 421e of the distal end portion 42e of the connecting member 42 in a direction perpendicular to the longitudinal direction of the clip projecting/retracting passage 18a (or the moving path of the connecting member 42).

The snap-fit members 43 may be each projected by a predetermined distance such that the snap-fit members 43 can cover and press against at least a part of the top surfaces 121b of the proximal end portions 12b of the clip 12 when the part of the top surfaces 121b of the proximal end portions 12b of the clip 12 are snap-fitted into the snap-fit members 43 during assembly process. In exemplary embodiments, the predetermined distance by which the snap-fit members 43 project is equal to the thickness (T) of the top (lateral) surfaces 122a (see FIG. 8B) of the proximal end portions 12b of the clip 12. In still other exemplary embodiments, the predetermined distance by which the snap-fit members 43 project is at least equal to the thickness (T) of the top (lateral) surfaces of the proximal end portions 12b of the clip 12, preferably greater than the thickness (T) of the top (lateral) surfaces of the proximal end portions 12b of the clip 12.

As shown in FIG. 8B, in this exemplary embodiment, the pair of snap-fit members 43 are formed to be line-symmetric with respect to an axial line C1 of the connecting member 42 (or the clip projecting/retracting passage 18a). The pair of snap-fit members 43 may be shaped like a pair of wings extending from the top surface 421e with a wingspan, which at least cover and press against part of, preferably the entire thickness (T) of, the top (lateral) surfaces 121b of the proximal end portions 12b of the clip 12 when the proximal end portions 12b are engaged by the pair of snap-fit members 43.

Figure 8C:
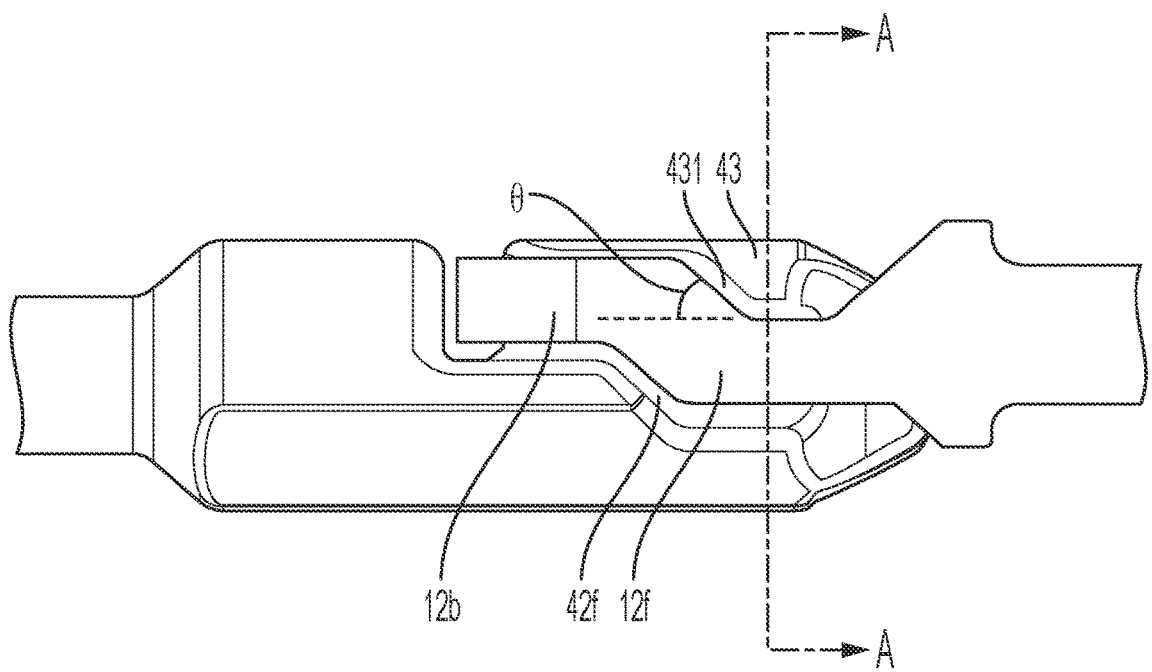

As shown in FIG. 8C, the snap-fit member 43 may include a stepped portion 431, as seen in a side view. The stepped portion 431 of the snap-fit member 43 is configured to be in conformity with the stepped portion 12f of the proximal end portions 12b of the clip 12 so as to achieve the snap fitting between the clip 12 and the connecting member 42. The stepped portion 431 can also be angled, as represented in FIG. 8C by angle θ. This invention is not limited to the angle disclosed in this exemplary embodiment, and any suitable angle for the stepped portion can be used, preferably from greater than 0 degrees to 90 degrees.

Figure 8D:
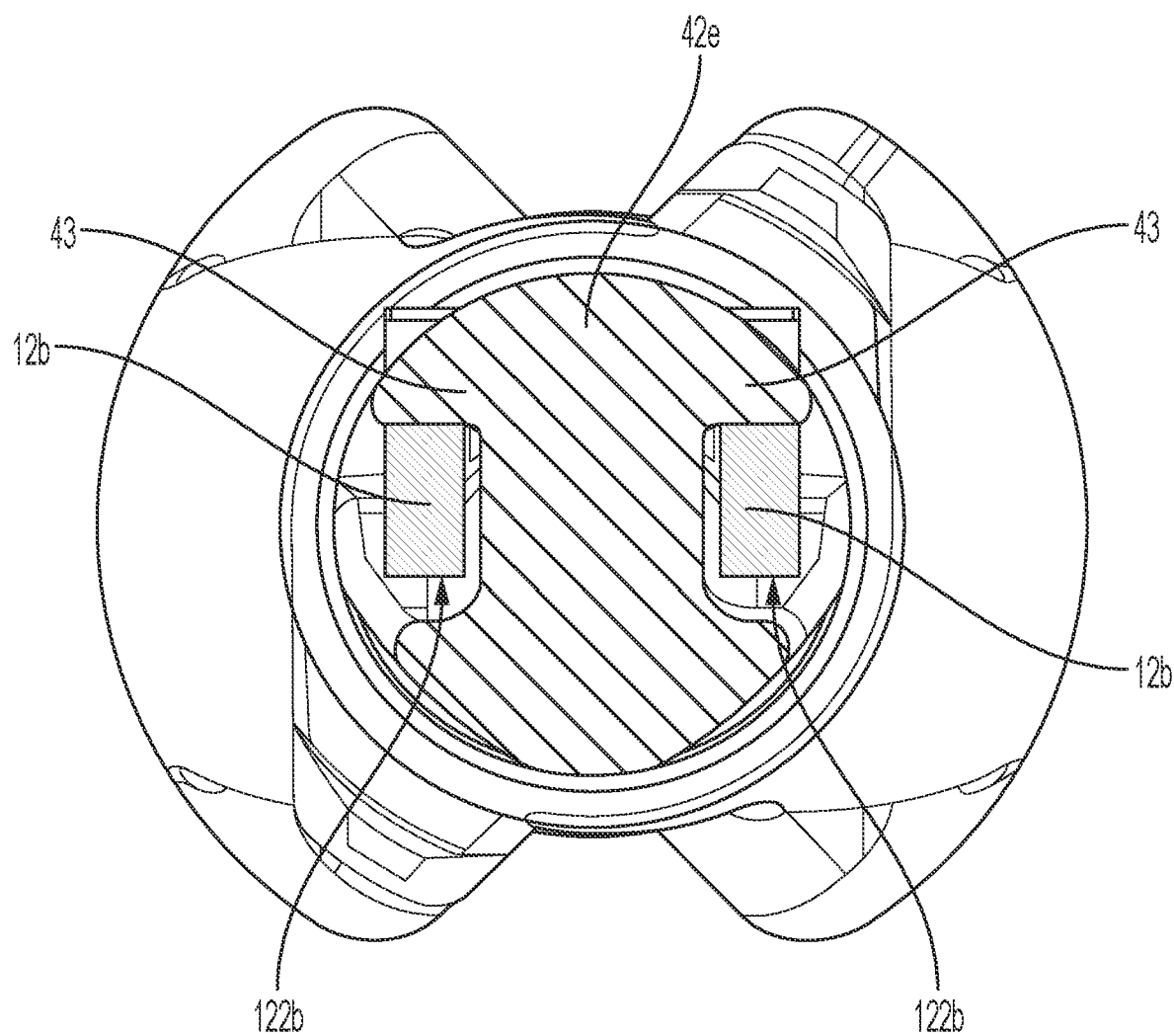

FIG. 8D is a transverse sectional view taken along a line A-A in FIG. 8C. As shown in FIG. 8D, the snap-fit members 43 fully overlap with areas of the top surfaces 121b where the snap-fit members 43 contact the proximal end portions 12b. The stepped portion 431 may include projections that may be assembled into recesses formed on the proximal end portions 12b, thereby snap-fitting the clip 12 and the connecting member 22 together.

The snap-fit members 43 of the invention are not limited to the above-described wing shape configuration, and any configuration, which is able to achieve the securable hooking of the clip 12 on the connecting member 42, is suitable to the invention.

Also, the snap-fit mechanism may further include any additional snap-fit member, which, for example, may be extended from the top surface 121b in a longitudinal direction of the connecting member 42, so that the additional snap-fit member can at least partially cover a connection part 122b that connects the proximal end portions 12b, thereby further strengthening the stability of the hooking of the clip 12 on the connecting member 42.

The snap fit members may be formed integrally with the connecting member 42, which may be formed by a molding process.

The snap-fit member may either be designed as a permanent snap or a multiple snap (which may be used multiple times). In the exemplary embodiment, the snap-fit members are permanent fits which cannot be disassembled because it is used in the clip unit as a disposable part.

As described above, by such a snap-fitting configuration, the connection between the clip 12 and the connecting member 22 can be regulated and stabilized, and the deviating force BF and the bending moment M can be effectively controlled, thereby preventing the proximal end portions 12b from coming off the distal end portion 22e and enhancing the hooking stability and also strengthening the pulling force of successfully breaking the breakable portion 22a.

Second Embodiment

Figure 9A:
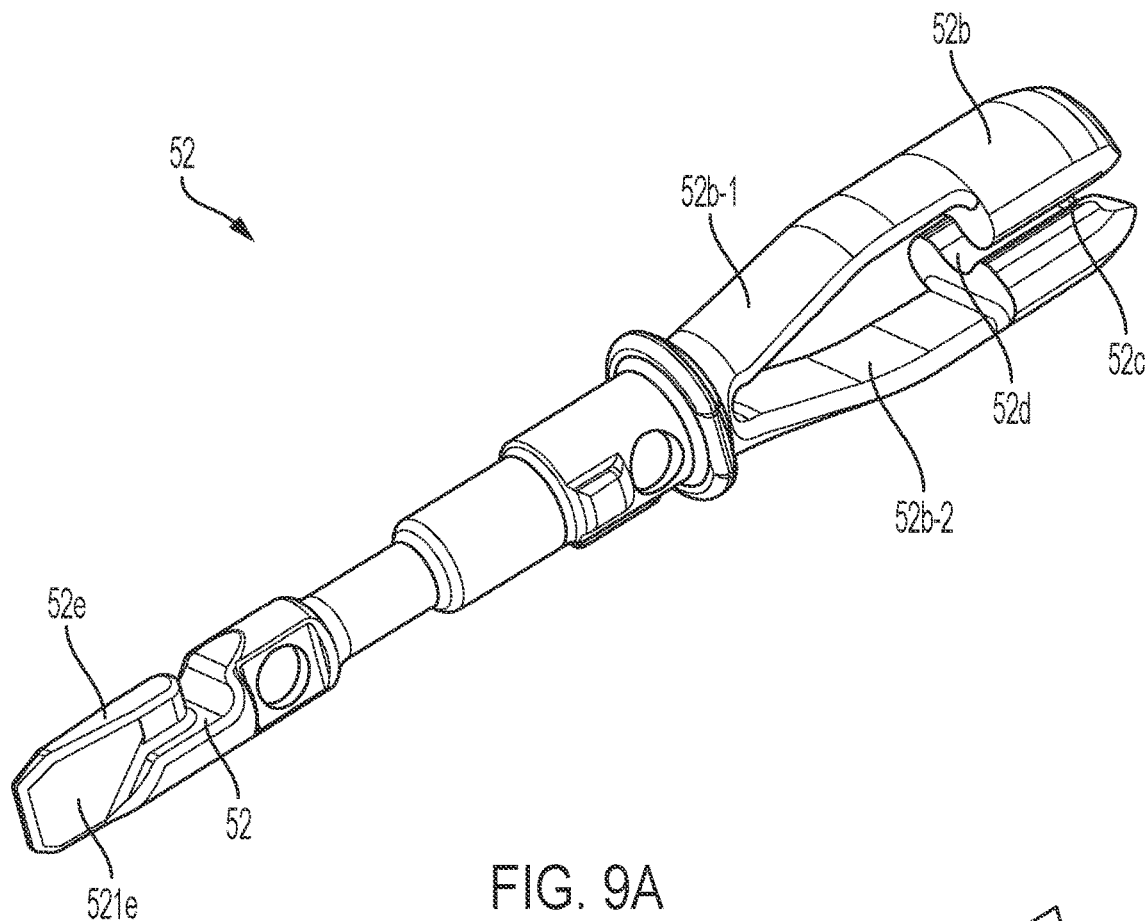
FIG. 9A is a perspective view schematically showing a connecting member of a clip unit associated with a clip delivery device according to a second exemplary embodiment.
Figure 9B:
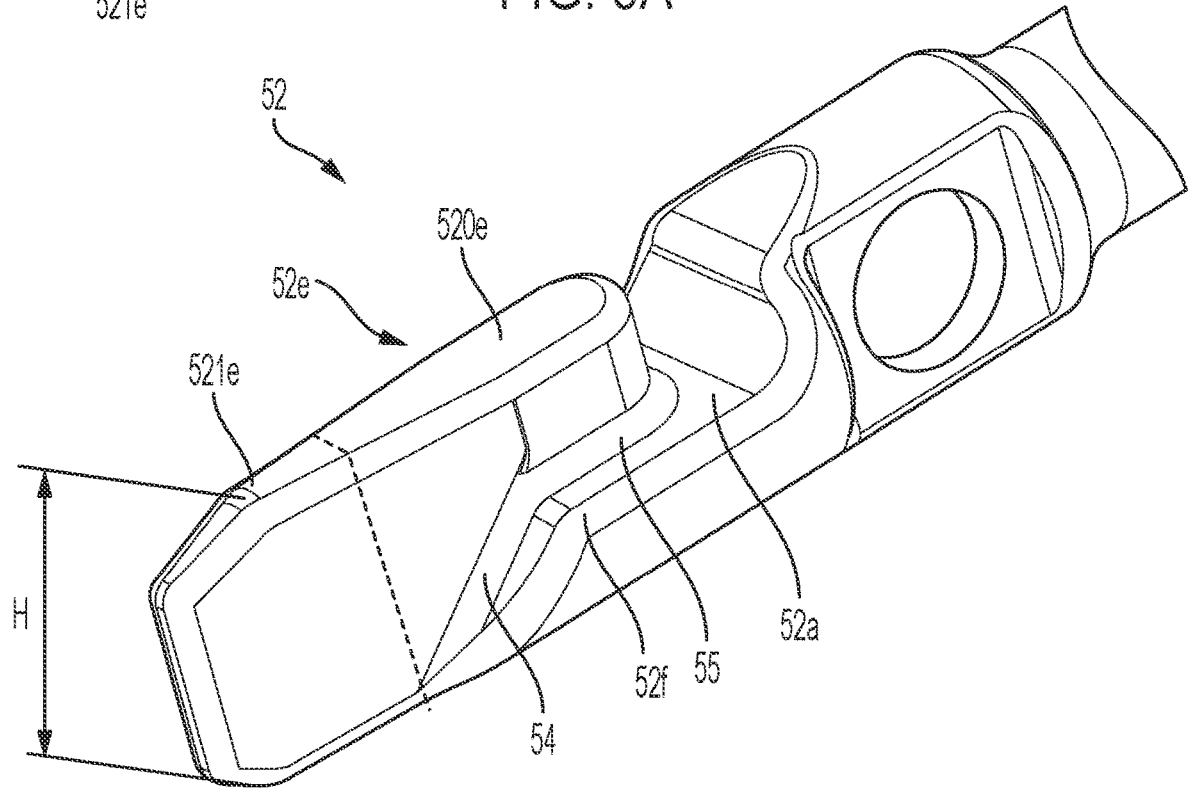
FIG. 9B is an enlarged view schematically showing an extended distal end portion of the connecting member according to the second exemplary embodiment.

FIG. 9A is a prospective view schematically showing a connecting member of a clip delivery device according to a second exemplary embodiment, and FIG. 9B is an enlarged view schematically showing the connecting member of FIG. 9A according to the second exemplary embodiment. The clip delivery device according to the second exemplary embodiment is different from the clip delivery devices of the first exemplary embodiment in that a clip unit has a different configuration.

The clip delivery device according to the second exemplary embodiment includes an extended type connecting member 52, which is disposed inside the clip holding member 18 and be movable in the extending direction of the clip holding member 18. The connecting member 52 includes a proximal end portion 52b that is connected to the clip connecting portion 16b of the clip operating part 16, and a distal end portion 52e which has surfaces forming a hook, by which the proximal end portions 12b of the slender arms 12c of the clip 12 are hooked on the connecting member 52.

The connecting member 52 is operated by the clip operating part 16 to move together with the clip 12 in the above described extending direction in the clip projecting/retracing passage 18a. The connecting member 52 has a breakable portion 52a, which can be broken when a pulling force larger than a predetermined value is applied thereto by the clip operating part 16. The breakable portion 52a has a reduced cross-sectional area (relative to other portions of the connecting member, particularly those portions closer to the proximal end portion 52b) to preferential break at this location.

The connecting member 52 may be formed by injection molding of resin material with high intensity, such as poly ether ether ketone (PEEK), liquid crystal polymer, nylon, and the like. The breakable portion 52a may be a notch or slit, which is cut from a part of an inner circumferential surface of the connecting member 52 outwardly in a radial direction of the clip holding member 18 and which extends in a direction crossing the extending direction of the clip projecting/retracting passage 18a. In this notch or slit, the proximal end portions 12b connected to each other in the slender arms 12c of the clip 12 are hooked by the distal end portion 52e of the connecting member 52.

As shown in FIG. 9B, the connecting member 52 further includes seating surfaces 54 and 55, which are formed to receive bottom (lateral) surfaces 122b (in FIG. 8D) of the proximal end portions 12b of the clip 12. The seating surfaces 54 and 55 are shaped to be in conformity with the configuration of the proximal end portions 12b, which are each formed to have a width that is equal to or greater than the thickness (T in FIG. 8B) of the proximal end portions 12b. The seating surfaces 54 and 55 form a stepped portion 52f corresponding to a stepped portion of the proximal end portions 12b. The seating surface 54 is formed inclined toward the bottom of the distal end portion 52e, and the seating surface 55 is formed on the base of the breakable portion 52a around the hook (the distal end portion 52e). Angles disclosed with respect to the stepped portion 42f can also be used for the stepped portion 52f.

The proximal end portion 52b of the connecting member 52 may be branched into two sections, the proximal end portion 52b being closer to the distal end portion 10a of the insertion part 10 than the breakable portion 52a. Two branched sections 52b-1 and 52b-2 are close to each other with a longitudinally extending division line 52c interposed therebetween, and a connection hole 52d extending along a longitudinal center line of the clip projecting/retracting passage 18a is formed in closely facing ends of the branched sections. In the connection hole 52d at the two branched sections of the proximal end portion 52b of the connecting member 52, a substantially conically shaped engaging portion 16c of a projecting end of a projection projecting from the distal end of the clip connecting portion 16b of the clip operating part 16 in the longitudinal direction of the clip operating part 16 is pressed in, so that a rotational connection between the two branched sections of the proximal end portion 52b of the connecting member 52 and the clip connecting portion 16b of the clip operating part 16 is achieved.

A part of the outer circumferential surface of the connecting member 52 may be flattened, and a part of the inner circumferential surface of the clip projecting/retracting passage 18a of the clip holding member 18, which corresponds to the flattened part of the outer circumferential surface of the connecting member 52, may be also flattened. The flattened part of the inner circumferential surface of the clip projecting/retracing passage 18a extends in a moving range of the flattened part of the outer circumferential surface of the connecting member 52 while the connecting member 52 moves in the clip projecting/retracting passage 18a.

A moving path of the clip 12 and the connecting member 52 inside the clip holding member 18 is adjacent to the inner surface of the clip holding member 18. In other words, a space (like the gap G1 as shown in FIG. 6B) exists between the outer surface of the connecting member 52 and the inner surface of the clip holding member 18. When the clip 12 and the connecting member 52, on which the clip 12 is hooked by the distal end portion 52e, are advanced or retracted inside the clip projecting/retracting passage 18a along the longitudinal direction thereof by the external operation portion 16a, rattling and associated relative motion occurs between the clip 12 and the connecting member 52, and a deviating force BF is applied around the base of the breakable portion 52a in a diameter expansion direction of the connecting member 52. Due to the deviating force BF, the proximal end portions 12b of the clip 12 becomes easily coming off the distal end portion 52e (the hook) of the connecting member 52. Also, the deviating force BF conflicts with the longitudinal movement of the connecting member 52, thereby decreasing the pulling force that is necessary to successfully break the breakable portion 52a.

Also, by pulling the clip 12 and the connecting member 52 by the external operating part 16, a bending moment M around the base of the breakable portion 52a is applied to the distal end portion 52e of the connecting member 52, thereby causing the distal end portion 52e to move in a diameter expansion direction of the connecting member 22. In this situation, another gap (like the gap G2 in FIG. 6C) between the base of the breakable portion 52a and a center of load received from the proximal end portions 12b of the clip 12 increases, which could cause an outer surface of the connecting member 52 to contact an inner surface of the clip projecting/retracting passage 18a. The bending moment M could negatively affect the longitudinal movement of the clip 12 and the connecting member 52, thereby decreasing the force of successfully breaking the breakable portion 52a.

In order to prevent the proximal end portions 12b of the clip 12 from coming off the distal end portion 52e (the hook) of the connecting member 52 and to effectively control (resist) the deviating force BF and the bending moment M, the connecting member 52 (as shown in FIG. 9B) further includes an extended body 521e which is extended from a main body 520e of the distal end portion 52e. Thus, the distal end portion 52e of this exemplary embodiment includes the extended body 521e and the main body 520e (shown and identified in FIG. 9B by a dashed line separating the extended body 521e and the main body 520e).

Figure 12:
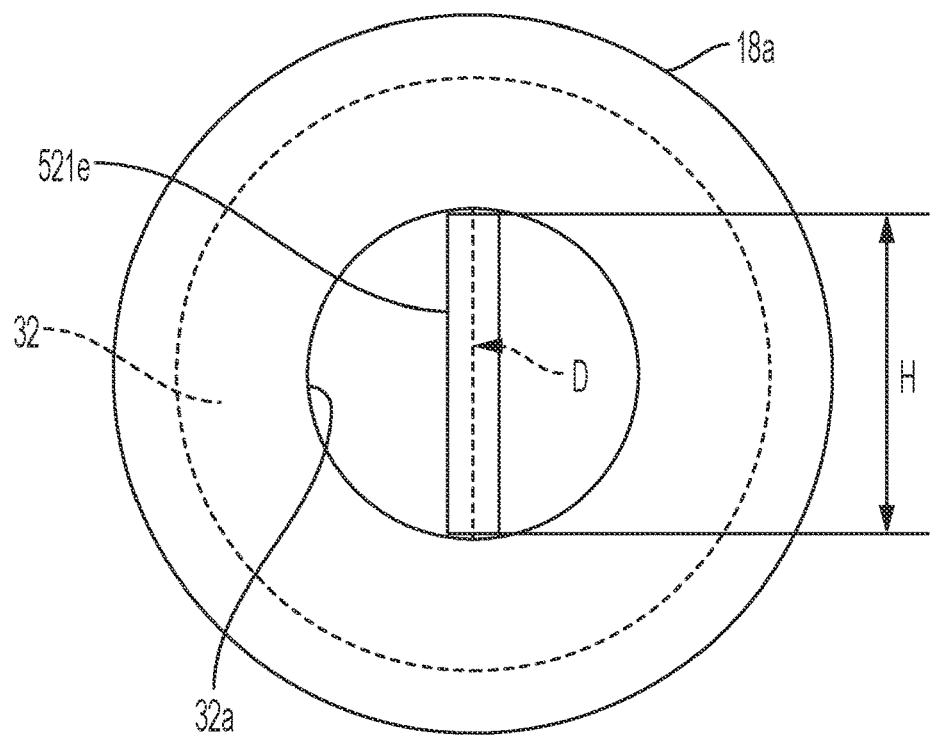
FIG. 12 schematically shows a transverse sectional view taken along a line B-B in FIG. 11 according to the second exemplary embodiment.

The extended body 521e has a height H which is substantially the same as a height of the main body 520e of the distal end portion 52e. As shown in FIG. 12 and as will further described below, the height H of the extended body 521e is set to be slightly shorter than an inner diameter D of the locking ring portion 32, such that when the extended body 521e passes through the locking ring portion 32, the extended body 521e comes into contact with the inner circumference surface of the locking ring portion 32, thereby preventing the connecting member 52 and the clip 12 which is hooked thereon from moving in a direction different from the longitudinal direction of the clip projecting/retracting passage 18a.

FIGS. 10A-10D are longitudinal section views showing sequential configurations of the clip delivery device in which the clip 12 is hooked on the connecting member 52 by the extended-type distal end portion 52e of FIGS. 9A and 9B.

Figure 10A:
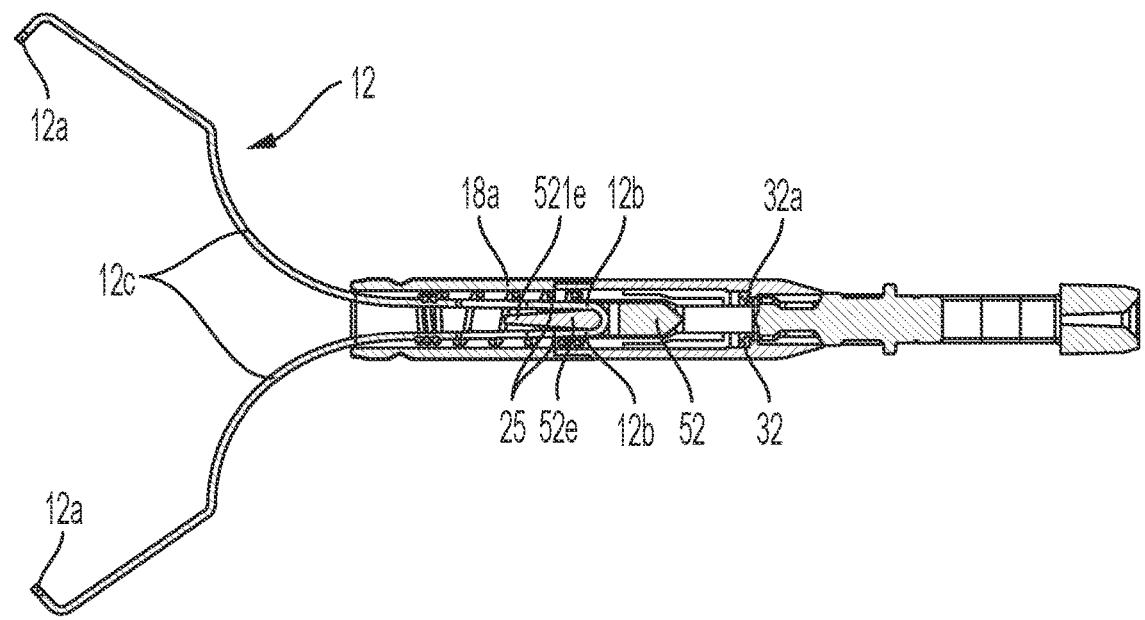
FIGS. 10A, 10B, 10C and 10D are longitudinal sectional views schematically showing configurations of a clip unit associated with a clip delivery device according to the second embodiment.

FIG. 10A shows one configuration in which the projected clip 12 opens the arms 12c outward in the radial direction of the clip projecting/retracing passage 18a. The connecting member 52 including the extended body 521e of the distal end portion 52e is located inside the clip projecting/retracing passage 18a, and the distal end portion 52e has a taper shape from a top view which gradually narrows toward the distal end of the clip projecting/retracing passage 18a in the longitudinal direction thereof.

In this configuration, the extended body 521e is located more distally than the locked portions 25, 26, and also located more distally than the locking ring portion 32. Alternatively, the locked portions 25, 26 and the locking ring portion 32 are located more proximally than the extended body 521e. Or the locked portions 25 are located closer to the locking ring portion 32 than the extended body 521e.

Figure 10B:
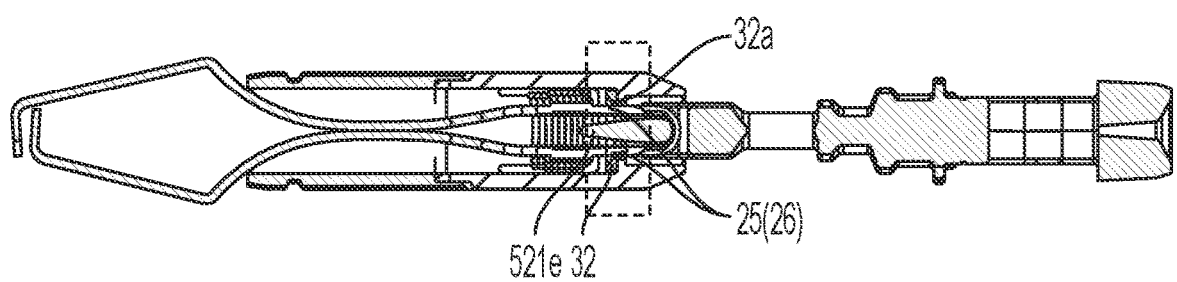

FIG. 10B shows a configuration in which the external operation portion 16a is operated to move the insertion part 10 in its longitudinal direction. As a result, when the arms 12c of the clip 12 are pulled into the clip projecting/retracting passage 18a of the clip holding member 18, the outside surfaces of the arms 12c slidingly contact the periphery of the opening of the clip projecting/retracting passage 18a at the projecting end of the clip holding member 18 and are pushed inward in the radial direction of the opening, so that the distal ends 12a of the arms 12c of the clip 12 can hold the desired region DR (not shown) of the desired tissue (not shown). The extended body 521e of the distal end portion 52e is pulled close to the locking ring portion 32 inside the clip projecting/retracting passage 18a. In this configuration, the distal end portion 52e including the extended body 521e is in contact with the inner circumferential surface 32a of the locking ring portion 32 during the pulling operation of the clip unit, thereby enhancing the stability of the movement of the clip unit and resisting the deviating force BF and the bending moment M that could negatively decrease the pulling force that is necessary to break the breakable portion 52a.

Figure 10C:
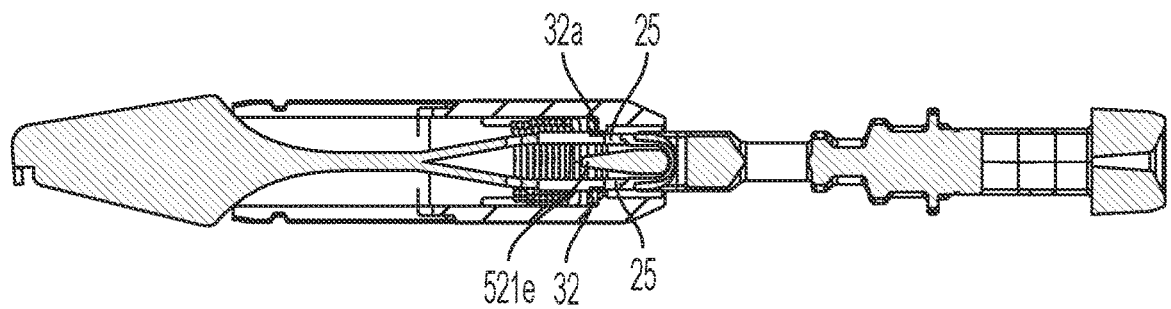

FIG. 10C shows a configuration in which the connecting member 52 is pulled by the external operation portion 16a furthermore, a pulling resistance generated in the desired region DR of the desired tissue and a frictional resistance generated on the outside surface of the arms 12c of the clip 12 with respect to the periphery of the opening of the clip projecting/retracing passage 18a are increased. These increased resistances and the pulling force applied to the base of the breakable portion 52a of the connecting member 52 could cause the rattling and associated relative motion between the clip 12 and the connecting member 52 at their connection area where the proximal end portions 12b are hooked by the distal end portion 52e. However, such rattling and associated relative motion can be effectively suppressed by the extended body 521e, because the extended body 521e remains in contact with the inner circumferential surface 32a of the locking ring portion 32 even when the connecting member 52 and the clip 12 are pulled by the clip operating part 16 to a position at which the pulling force reaches a predetermined value by which the breakable portion of the connecting member is to be broken. In this configuration, the extended body 521e is still located more distally than the locking ring portion 32.

Figure 11:
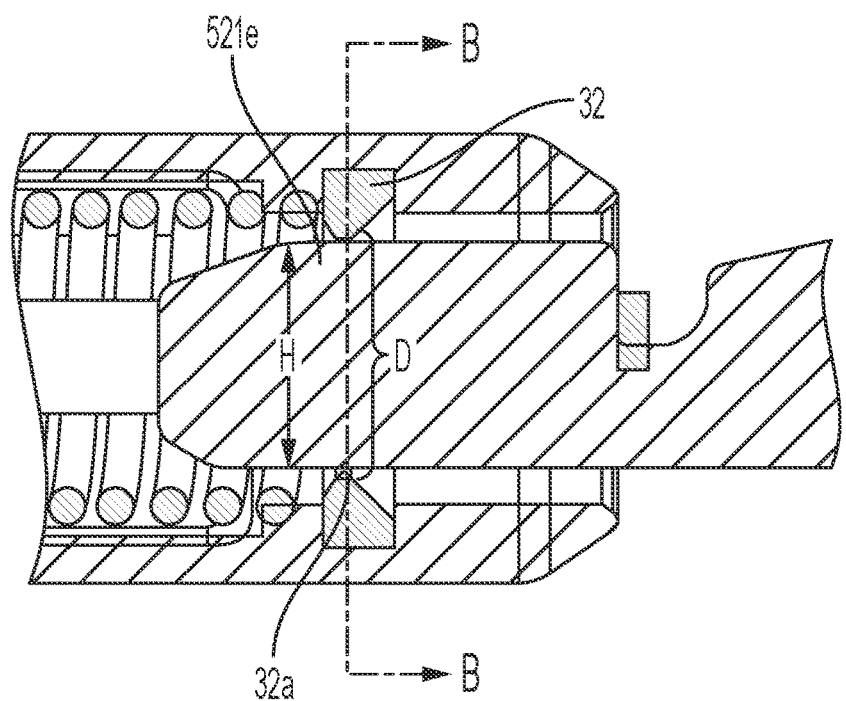
FIG. 11 is a cross-sectional view schematically illustrating a structure of the clip unit of FIG. 10C according to the second exemplary embodiment.

FIG. 11 shows an enlarged sectional view schematically illustrating the configuration of the extended-type connecting member of FIG. 10C. As shown in FIG. 11, the extended body 521e of the distal end portion 52e of the connecting member 52 has a tapered shape so as not to regulate the movement of the locked portions (protrusions) 25 and 26 as the protrusions 25 and 26 pass through the locking ring portion 32. The tapered shape of the expanded body 521e extends in the axial direction of the clip projecting/retracting passage 18a. Also the extended body 521e has the height H, which is set to be slightly shorter than the inner diameter D of the locking ring portion 32 so that the extended body 521e can be in contact with the inner circumferential surface 32a of the locking ring portion 32. As shown in FIG. 12, the contact between the extended body 521e and the inner circumference surface of the locking ring portion 32 can prevent the connecting member from moving in any direction that is different from the longitudinal direction of the clip projecting/retracting passage 18a, thereby effectively suppressing the rattling and associated relative motion between the clip 12 and the connecting member 52. Also, the contact between the extended body 521e and the inner circumference surface of the locking ring portion 32 can effectively resist against the deviating force BF and the bending moment M which could decrease the pulling force necessary to successfully break the breakable portion 52a.

Figure 10D:
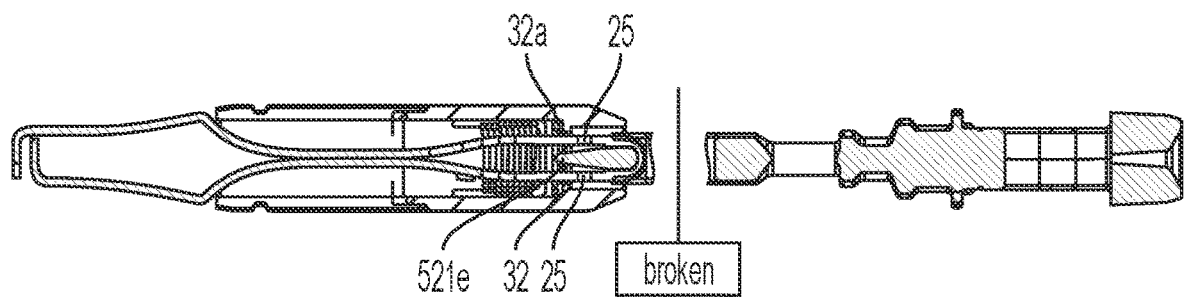

FIG. 10D shows a configuration in which the breakable portion 52a is broken, after the connecting member 52 is being pulled furthermore into the clip projecting/retracting passage 18a of the clip holding member 18, the pulling force applied to the base of the breakable portion 52a of the connecting member 52 by the clip operating part 16 reaches a predetermined value that is set to break the base of the breakable portion 52a.

Figure 13:
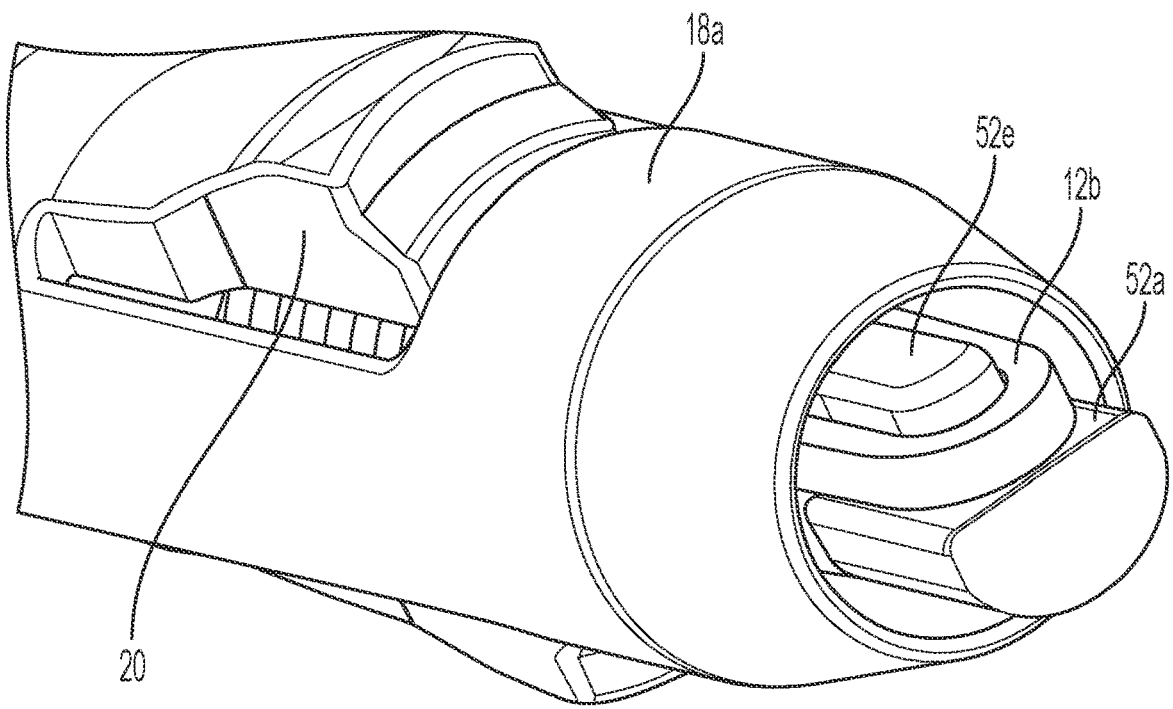
FIG. 13 is an exemplary view after a breakable portion of the clip unit is successfully broken according to one exemplary embodiment.

As shown in FIG. 13, after the breakable portion 52a is successfully broken, the distal end portion 52e is separate from the connecting member 52, and is left with the clip 12 in the cavity of the living body.

While various embodiments of the disclosed technology have been described above, it should be understood that they have been presented by way of example only, and not of limitation. Likewise, the various diagrams may depict an example schematic or other configuration for the disclosed technology, which is done to aid in understanding the features and functionality that can be included in the disclosed technology. The disclosed technology is not restricted to the illustrated example schematic or configurations, but the desired features can be implemented using a variety of alternative illustrations and configurations. Indeed, it will be apparent to one of skill in the art how alternative functional, logical or physical locations and configurations can be implemented to implement the desired features of the technology disclosed herein.

Although the disclosed technology is described above in terms of various exemplary embodiments and implementations, it should be understood that the various features, aspects and functionality described in one or more of the individual embodiments are not limited in their applicability to the particular embodiment with which they are described, but instead can be applied, alone or in various combinations, to one or more of the other embodiments of the disclosed technology, whether or not such embodiments are described and whether or not such features are presented as being a part of a described embodiment. Thus, the breadth and scope of the technology disclosed herein should not be limited by any of the above-described exemplary embodiments.

Terms and phrases used in this document, and variations thereof, unless otherwise expressly stated, should be construed as open ended as opposed to limiting. As examples of the foregoing: the term "including" should be read as meaning "including, without limitation" or the like; the term "example" is used to provide exemplary instances of the item in discussion, not an exhaustive or limiting list thereof; the terms "a" or "an" should be read as meaning "at least one," "one or more" or the like; and adjectives such as "conventional," "traditional," "normal," "standard," "known" and terms of similar meaning should not be construed as limiting the item described to a given time period or to an item available as of a given time, but instead should be read to encompass conventional, traditional, normal, or standard technologies that may be available or known now or at any time in the future. Likewise, where this document refers to technologies that would be apparent or known to one of ordinary skill in the art, such technologies encompass those apparent or known to the skilled artisan now or at any time in the future.

The presence of broadening words and phrases such as "one or more," "at least," "but not limited to" or other like phrases in some instances shall not be read to mean that the narrower case is intended or required in instances where such broadening phrases may be absent.

Additionally, the various embodiments set forth herein are described in terms of exemplary schematics, block diagrams, and other illustrations. As will become apparent to one of ordinary skill in the art after reading this document, the illustrated embodiments and their various alternatives can be implemented without confinement to the illustrated examples. For example, block diagrams and their accompanying description should not be construed as mandating a particular configuration.

What is claimed is:

1. A clip unit, comprising:
a clip translatable between a retracted position and a projected position, wherein the clip includes two arms connected at a proximal end portion of the clip;
a tube having an interior space configured to store the proximal end portion of the clip when the clip is in the retracted position; and
a connecting member having a hook configured to attach the proximal end portion of the clip to the connecting member;
wherein the hook includes:
a first protrusion protruding in a first width direction of the hook, the first protrusion having a first surface, and
a second protrusion protruding in a second width direction opposite to the first width direction, the second protrusion having a second surface,
wherein, in a first plane including at least a part of the first surface and at least a part of the second surface and intersecting a longitudinal direction of the hook, a first length between a most outward end of the first surface and a most outward end of the second surface is larger than a second length between inner surfaces of the two arms, and
wherein, in the first plane and in a circumferential direction of the hook, the first surface is oriented toward a part of the proximal end portion of the clip to suppress rattling that occurs when the proximal end portion of the clip is pulled into the tube.

2. The clip unit according to claim 1, wherein the hook includes a snap-fit member, and
wherein the snap-fit member is formed integrally with the hook.

3. The clip unit according to claim 1, wherein the hook includes an extended body located at a distal end side of the hook,
wherein the clip includes a clip protrusion outwardly protruding in a radial direction of the hook,
wherein the tube includes a tube protrusion inwardly protruding in the radial direction from an inner circumferential surface of the tube, and
wherein the clip protrusion is located more proximally relative to the extended body of the hook.

4. The clip unit according to claim 3, wherein the tube protrusion is located more proximally relative to a distal end of the extended body of the hook when the clip protrusion is located proximally relative to the tube protrusion and when the clip protrusion engages the tube protrusion.

5. The clip unit according to claim 4, wherein an outer circumferential surface of the extended body of the hook contacts an inner circumferential surface of the tube protrusion when the clip is closed and when the clip protrusion is located proximally relative to the tube protrusion.

6. The clip unit according to claim 3, wherein the extended body of the hook has a height that is set to be slightly shorter than an inner diameter of the tube protrusion.

7. The clip unit according to claim 1, wherein the proximal end portion of the clip includes:
a first clip surface having a first clip width in a first direction;
a second clip surface having a second clip width in a second direction perpendicular to the first direction. wherein the second clip width is smaller than the first clip width; and
a third clip surface having a third clip width in the second direction and the third clip surface opposing to the second clip surface, wherein the third clip width is smaller than the first clip width,
wherein the first surface is configured to receive the second clip surface.

8. The clip unit according to claim 7, wherein at least one stepped portion is formed by the third clip surface.

9. The clip unit according to claim 8, wherein the hook includes a seating surface, and
wherein the at least one stepped portion formed by the third clip surface is formed by the seating surface.

10. The clip unit according to claim 7, wherein the hook includes a seating surface configured to receive the third clip surface.

11. The clip unit according to claim 10, wherein the seating surface is located proximally to the first surface.

12. The clip unit according to claim 1, wherein the hook has a third surface separated from the first surface, and
wherein, in the circumferential direction, the part of the proximal end portion of the clip is located between the first surface and the third surface to suppress rattling that occurs when the proximal end portion of the clip is pulled into the tube.

13. The clip unit according to claim 12, wherein the third surface has a first step protruding toward the first surface in the circumferential direction of the hook, and
wherein the clip has a second step to engage with the first step of the third surface in the circumferential direction.

14. The clip unit according to claim 12, wherein the proximal end portion of the clip has a first contact surface and a second contact surface that is larger than the first contact surface;
wherein the first contact surface is configured to contact with the first surface of the hook; and
wherein the second contact surface is configured to contact with the third surface of the hook.

15. The clip unit according to claim 12, wherein the third surface is offset from the first surface in the longitudinal direction of the hook and the third surface is located proximally relative to the first surface.

16. The clip unit according to claim 12, wherein the first plane includes the first surface and does not include the third surface.

17. The clip unit according to claim 1, wherein the clip has a clip protrusion located distally relative to the first protrusion of the hook.

18. The clip unit according to claim 1, wherein the hook has an intermediate portion,
wherein the intermediate portion is located between the two arms at the proximal end portion of the clip, and
wherein, in the first plane, the first protrusion protrudes from the intermediate portion in the first width direction.

19. The clip unit according to claim 18, wherein
the second protrusion protrudes from the intermediate portion in the second width direction.

20. A clip unit delivery device, comprising:
the clip unit according to claim 1,
an elongated portion configured to attach to a proximal end of the tube, wherein the elongated portion is configured to insert the hook into the tube; and
an operating portion coupled to a proximal end of the elongated portion, wherein the operating portion is configured to translate the clip between the retracted position and the projected position.

* * * * *